United States Patent [19]

Debe

[11] Patent Number: 5,238,729
[45] Date of Patent: Aug. 24, 1993

[54] SENSORS BASED ON NANOSSTRUCTURED COMPOSITE FILMS

[75] Inventor: Mark K. Debe, Stillwater, Minn.

[73] Assignee: Minnesota Mining and Manufacturing Company, St. Paul, Minn.

[21] Appl. No.: 681,332

[22] Filed: Apr. 5, 1991

[51] Int. Cl.$^5$ ............................................. B32B 5/00
[52] U.S. Cl. ................................... 428/245; 428/142; 428/143; 428/221; 428/223; 428/323; 428/336; 428/338; 430/56
[58] Field of Search ............... 428/245, 142, 143, 221, 428/323, 336, 338; 430/56

[56] References Cited

U.S. PATENT DOCUMENTS

| | | | |
|---|---|---|---|
| 3,045,198 | 7/1962 | Dolan et al. | 338/13 |
| 3,820,958 | 6/1974 | Cheng et al. | 436/151 |
| 3,969,545 | 7/1976 | Slocum | 427/163 |
| 4,148,294 | 4/1979 | Scherber et al. | 126/270 |
| 4,155,781 | 5/1979 | Diepers | 437/2 |
| 4,209,008 | 6/1980 | Kemkey et al. | 126/714 |
| 4,215,170 | 7/1980 | Oliva | 428/328 |
| 4,224,595 | 9/1980 | Dolan | 338/34 |
| 4,252,864 | 2/1981 | Coldren | 428/571 |
| 4,262,072 | 4/1981 | Wendling et al. | 430/14 |
| 4,313,338 | 2/1982 | Abe et al. | 73/23 |
| 4,340,276 | 7/1982 | Maffitt et al. | 350/164 |
| 4,396,643 | 8/1983 | Kuehn et al. | 427/160 |
| 4,568,598 | 2/1986 | Bilkadi et al. | 428/141 |
| 4,631,952 | 12/1986 | Donaghey | 73/23 |
| 4,674,320 | 6/1987 | Hirschfeld | 73/23 |
| 4,678,695 | 7/1987 | Tung et al. | 428/120 |
| 4,774,122 | 9/1988 | Adler | 428/156 |
| 4,785,064 | 11/1988 | Hegel | 526/261 |
| 4,812,352 | 3/1989 | Debe | 428/142 |
| 4,906,440 | 3/1990 | Kolesar, Jr. | 422/98 |
| 4,908,258 | 3/1990 | Hernandez | 428/198 |
| 4,986,496 | 1/1991 | Marentic et al. | 244/130 |
| 5,039,561 | 11/1988 | Debe | 427/255 |

OTHER PUBLICATIONS

International Search Report.
Annex to the International Search Report.
Patent Abstract of Japan, vol. 8, No. 208 (P-302)(1645) Sep. 21, 1984.
Cowan et al., "The Organic Solid State," Chem. and Eng. News, Jul. 21, 1986, pp. 28-45.
Lee et al., "Measurement and Modelling of the Reflectance-Reducing Properties of Gradient Index Microstructured Surfaces," Photographic Science and Engineering, vol. 24, No. 4, Jul./Aug. 1980 pp. 211-216.
Rushau et al., "0-3 Ceramic/Polymer Composite Chemical Sensors," Sensors and Actuators, 20 (1989) pp. 269-275.
Oehrlein et al., "Study of sidewall passivation and microscopic silicon roughness phenomena in chlorine-based reactive ion etching of silicon trenches", J. Vac. Sci. Technol. B 8 (6), Nov./Dec. 1990 pp. 1199-1211.
Ohnuma et al., "Amorphous Ultrafine Metallic Particles Prepared by Sputtering Method," Rapidly Quenched Metals (Elsevier Science Publishers B.V., 1985, Steeb and Warlimont (eds.)) pp. 1117-1124.
Bartlett et al., Conducting Polymer Gas Sensors, Sensors and Actuators, 20 (1989), pp. 287-292.
Floro et al., "Ion-Bombardment-Induced Whisker For- (List continued on next page.)

*Primary Examiner*—Patrick J. Ryan
*Assistant Examiner*—Richard C. Weisberger
*Attorney, Agent, or Firm*—Gary L. Griswold; Walter N. Kirn; Carolyn V. Peters

[57] ABSTRACT

An electrically reactive composite article comprising a random or regular array of microstructures partially encapsulated within an encapsulating layer, microstructures each comprising a whisker-like structure, optionally having a conformal coating enveloping the whisker-like structure is described. The composite article is useful as an electrically conducting component of a circuit, antenna, microelectrode, reactive heater, and multimode sensor to detect the presence of vapors, gases, or liquid analystes.

14 Claims, 9 Drawing Sheets

OTHER PUBLICATIONS mation on Graphite," J. Vac. Sci. Technol A 1(3), Jul.-Sep. 1983, pp. 1395-1402.

Debe et al., "Effect of Gravity on Copper Phthalocyanine Thin Films III:," Thin Solid Films, 186 (1990) pp. 327-347.

Debe et al., "Vacuum vapor deposited thin films of a perylene dicarboximide derivative:," J. Vac. Sci. Technol A 6 (3), May/Jun. 1988, pp. 1907-1911.

Kam et al., "Summary Abstract: Dramatic variation of the physical microstructure of a vapor deposited organic thin film," J. Vac. Sci. Technol. A, vol. 5, No. 4, Jul./Aug. 1987 pp. 1914-1916.

Dirks et al., "Columnar Microstructure in Vapor-Deposited Thin Films," Thin Solid Film, 47 (1977) pp. 219-233.

Sadaoka et al., "Effects of morphology on $NO_2$ detection in air at room temperature with phthalocyanine thin films," J. of Mat'l Sci., 25 (1990), pp. 525-568.

Katritzky et al., "New Sensor Coatings For The Detection of Atmospheric Contaminants and Water".

Katritzky et al., "The Development of New Microsensor Coatings and a Short Survey of Microsensor Technology," Analytical Chemistry, vol. 21, issue 2, (1989) pp. 83-113.

Snow et al., "Synthesis and Evaluation of Hexafluorodimethylcarbinol Functionalized Polymers as Saw Microsensor Coatings," Polymer Preprints 30 (2), pp. 213-214, (1989).

Morrison et al., "Polynuclear Aromatic Compounds," Organic Chemistry, Third Edition, pp. 967-1026.

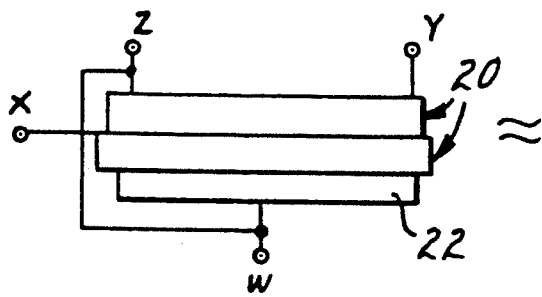
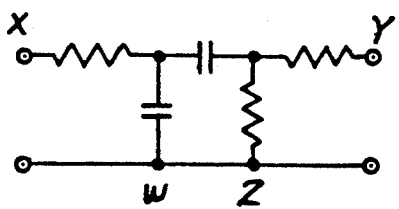
FIG. 4A  FIG. 4B
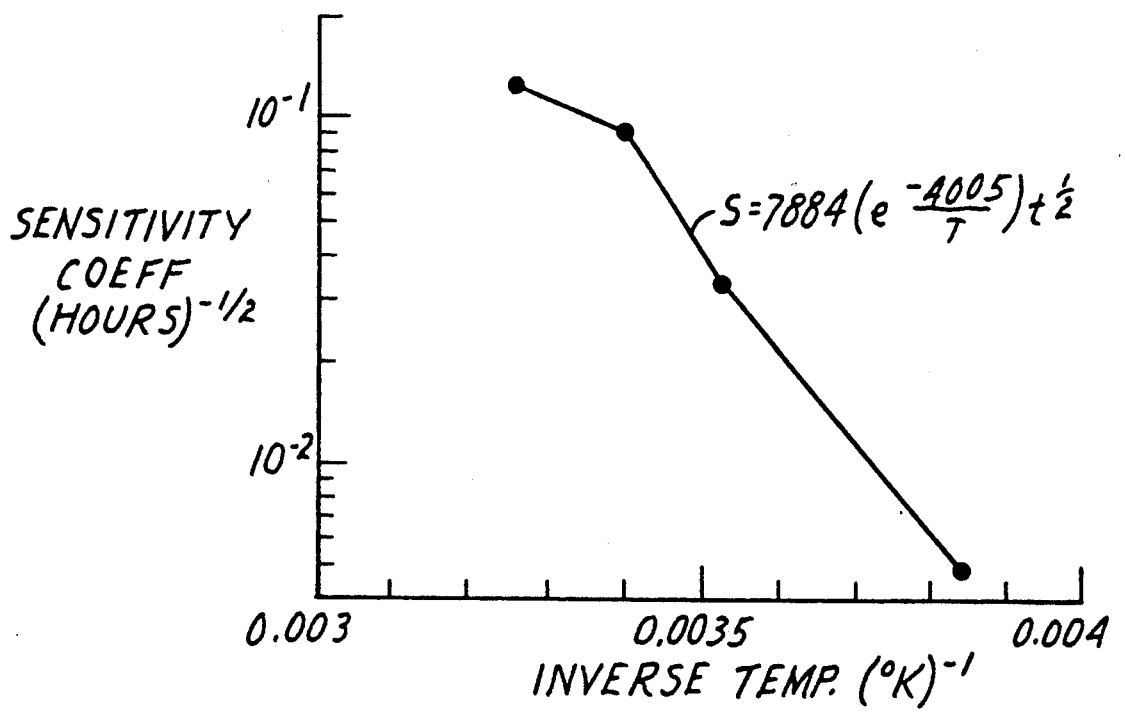
FIG. 18

SENSORS BASED ON NANOSSTRUCTURED COMPOSITE FILMS

BACKGROUND OF THE PRESENT INVENTION

1. Field of the Invention

This invention relates to a composite article comprising randomly or regularly arrayed oriented microstructures partially encapsulated within a layer, in particular to the method of making the same and to the use of the composite article as an electrically conducting polymer, thin film resonant circuit, antenna, microelectrode or resistive heater, and as a multimode sensor to detect the presence of vapors, gases, or liquid analytes.

2. Background Art

Composite articles containing or exhibiting a layered structure have been prepared by many different types of chemical and physical deposition processes.

For example, U.S. Pat. No. 4,812,352 discloses an article comprising a substrate having a microlayer (microstructured-layer) that comprises uniformly oriented, crystalline, solid, organic microstructures, several tens of nanometers in cross-section and a method of making the same. Further, '352 teaches optionally conformal coating the microlayer and encapsulating the conformal-coated microlayer.

Dirks et al. in "Columnar Microstructures in Vapor-Deposited Thin Films," *Thin Solid films,* vol. 47, (1977), pgs 219-33 review several methods known in the art that can yield columnar microstructures, however, as Dirks et al. point out the structures are not a desirable or a sought-after outcome of vapor-deposition.

U.S. Pat. No. 3,969,545 describes a vacuum deposition technique that can produce organic or inorganic microstructures.

Floro et al. in "Ion-Bombardment-Induced Whisker Formation of Graphite," *J. Vac. Sci. Technol. A.* vol. 1, no. 3, July/September (1983) pgs 1398-1402 describe graphite whisker-like structures produced by an ion-bombardment process.

Flexible conducting media known in the art, typically having a layered structure, exist in a variety of distinct formats. For example, U.S. Pat. No. 4,674,320 discloses a conducting powder-like material, such as carbon, dispersed throughout a polymeric binder at concentrations sufficient to enable conduction by charge transfer from particle to particle. Such an arrangement results in an isotropicly conducting sheet, that is, resistivity perpendicular to the plane of the sheet is the same as the in-plane resistivity.

Bartlett et al., *Sensors and Actuators,* vol. 20, pg 287, 1989, disclose a conductive polymer film made by electrochemical polymerization. Resistivities of these polymer films are three-dimensionally isotropic and tend to be relatively high.

Other examples known in the art teach an article comprising a conducting layer applied to a flexible polymer sheet by vacuum coating processes, electrochemical or electroless plating processes, printing, particle embedding and the like. However, in these cases, the conductive coating, for example, a solid metallic layer, will have a low resistivity and is not easily controllable. Additionally, since the conductive layer is on the surface of a polymer substrate, adhesion of the conductive layer to the polymer substrate is often a problem. The adhesion problem is particularly apparent when the conducting layer is carrying current. If a very thin or discontinuous conductive layer is applied to the polymer substrate to increase the surface resistivity, the power carrying capability of the conductive layer tends to be compromised and the problem of adhesion tends to be exacerbated.

Electrical properties are useful as sensors, however, most prior art gas and vapor sensors are based on many of the prior art layered structures. The sensor media can be thin or thick film devices utilizing either surface acoustic wave (SAW) technology or chemiresistors incorporating solid electrolytes, polymers with bulk gas sensitivity, metal or semiconductor (inorganic or organic) thin films, or homogeneous dispersions of conducting particles in insulating matrices.

Generally, sensors based on SAW technology are costly to manufacture and tend to be used only for reversible sensing. They are generally not used for nonreversible sensors, such as dosimetry monitoring, see Snow et al., "Synthesis and Evaluation of Hexafluorodimethyl carbinol Functionalized Polymers as SAW Microsensor Coatings," Polymer Reprints, 30(2), 213 (1989); Katritzky et al., "The Development of New Microsensor Coatings and a Short Survey of Microsensor Technology," Analytical Chemistry 21(2), 83 (1989).

On the other hand, chemiresistor based sensors tend to be reversible or nonreversible depending on the chemical and physical composition of the sensing medium, see Katritzky et al., "New Sensor Coatings for the Detection of Atmospheric Contaminants and Water," Review of Heteroatom Chemistry, 3, 160 (1990). Generally, the prior art sensing media exhibit isotropic or homogeneous gas sensing properties. Media having an isotropic sensing property display the same resistivity in all directions of the media. Such media are typically capable of only a single mode of detection. In contrast, media having an anisotropic impedance sensing property display different in-plane and out-of-plane gas sensing impedances. Thus, anisotropic media permit multi-mode operation.

Generally, conduction through chemiresistor devices occurs between conducting particles dispersed throughout the media. For example, U.S Pat. No. 4,674,320 teaches a chemiresistive gas sensor comprising a layer of organic semiconductor disposed between two electrodes, wherein dispersed within the layer of organic semiconductor is a high conductivity material in the form of very small particles, or islands. Adsorption of a gaseous contaminant onto the layer of organic semiconductor or modulates the tunneling current.

U.S. Pat. No. 4,631,952 discloses an apparatus and a method for sensing organic liquids, vapors, and gases that includes a resistivity sensor means comprising an admixture of conductive particles and a material capable of swelling in the presence of the liquid, gas, or vapor contaminant.

Ruschau et al., "0-3 Ceramic/Polymer Composite Chemical Sensors," *Sensors and Actuators,* vol. 20, pgs 269-75, (1989) discloses a composite article consisting of carbon black and vanadium oxide conductive fillers in polyethylene, a polyurethane, and polyvinyl alcohol for use as chemical sensors. The polymer matrices swell reversibly in the presence of liquid and gaseous solvents, disrupting the conductive pathway and proportionally increasing the resistance.

U.S. Pat. No. 4,224,595 discloses an adsorbing type sensor having electrically conductive particles embedded in a surface, forming an electrically conductive path through the sensor.

U.S. Pat. No. 4,313,338 discloses a gas sensing device comprising a gas sensing element comprising a gas-sensitive resistive film formed of an aggregate of ultrafine particles of a suitable material deposited on the surface of a substrate of an electrical insulator formed with electrodes.

U.S. Pat. No. 3,820,958 discloses an apparatus and a method for determining the presence of hydrogen sulfide in a gas mixture. Silver is deposited on a thin dielectric film. Electrical resistance across the film before and after exposure of the film to hydrogen sulfide containing gas mixture is utilized to determine the amount of hydrogen sulfide present.

U.S. Pat. No. 4,906,440 discloses a sensor for a gas detector comprising a metallic/metallic oxide gas sensitive discontinuous film. The gas changes the conductivity of the film and causes the RC network to react.

U.S. Pat. No. 3,045,198 discloses a detection device comprising an electrical element sensitive to exposure to liquids, vapors or gases. The detection element includes a broad and long base having an electrically non-conductive, relatively resilient surface on which is anchored a stratum of exposed electrically conductive discrete adsorbent particles.

Sadaoka et al., Effects of Morphology on $NO_2$ Detection in Air at Room Temperature with Phthalocyanine Thin Films," J. of Mat'l Sci. 25, 5257 (1990) disclose that crystal size in films is affected by the nature of the substrate, ambient atmosphere, and annealing time. The variations of the crystals can effect the detection of $NO_2$ in air.

SUMMARY OF THE PRESENT INVENTION

Briefly, this invention provides a composite article with an electrically conductive surface comprising a layer having a dense array of discrete, oriented microstructures partially encapsulated and optionally having a conformal coating wherein one end of the microstructures is exposed and coincident with the conductive surface. The conformal coating, preferably is a conducting material. The encapsulant, is preferably a dielectric. Advantageously, the anisotropic structure of the composite article provides anisotropic impedance, that is, the impedance parallel to the surface plane of the composite article is resistive, while the impedance perpendicular to the surface plane of the article is predominantly capacitive.

In another aspect, a resonant circuit is described wherein the composite article provides the resistive (R) and capacitive (C) component of the circuit. Advantageously, the resonant circuit can be constructed as a low-pass filter, a high-pass filter, a band-pass filter and the like. Furthermore, the composite article can be fabricated such that the conducting layer is formed in patterns suitable for building electronic circuits. This is achieved, by depositing the crystalline microstructures in patterns, or conformally coating the microstructures through a mask, or by encapsulating the coated microstructures through a mask, or by any combination of the above.

In yet another aspect of the present invention, a multimode sensor is described. The unique construction of the composite article enables selection of the conformal coating and the encapsulant for their responses to a particular analyte molecule of interest. The effect of gas/vapor/liquid molecules on the multimode sensor is detected by monitoring the changes in the composite article's electrical properties, that is the resistance and the capacitance.

In this application:

"whisker-like structure" refers to individual repeating units such as, for example, material structures, whiskers, rods, cones, cylinders, laths, pyramids and other regular or irregular geometric shaped structures;

"microstructure" refers to the whisker-like structure that has been conformally coated;

"microstructured-layer" refers to a layer formed by all the microstructures taken together;

"conformal-coated" means a material is deposited onto the sides and an end of each whisker-like structure element to envelope the element such that the deposited material conforms to the shape of the whisker-like structure element;

"uniformly oriented" means the microstructures are approximately perpendicular to the surface of the substrate;

"solidified" means the encapsulant undergoes a change in state, typically from a liquid or liquid-like phase to a more rigid, solid, or solid-like phase, such as may occur as a result of drying, chemical setting, cooling, freezing, gelling, polymerization, etc.;

"continuous" means coverage of a surface without interruption of the coating;

"discontinuous" means coverage of a surface wherein there is periodic or non-periodic interruption of the coating;

"uniform" with respect to size, means that the major dimension of the cross-section of the individual microstructures varies no more than about $\pm 25\%$ from the mean value of the major dimension and the minor dimension of the cross-section of the individual microstructures varies no more than about $\pm 25\%$ from the mean value of the minor dimension;

"areal number density" means the number of microstructures per unit area;

"gas" means a state of matter existing in the gaseous state at standard temperature and pressure, but can be liquified by pressure; and "vapor" means an air dispersion of molecules of a substance that is liquid or solid in its normal state, that is at standard temperature and pressure, sometimes called fumes.

BRIEF DESCRIPTION OF THE DRAWINGS

FIGS. 4 (a) and (b) illustrate an alternative "series" configuration with band-pass characteristics and a simplified equivalent circuit.

FIG. 18 is a solid state diffusion model representation of sensitivity versus time data from FIG. 12.

DETAILED DESCRIPTION OF THE PREFERRED EMBODIMENT

The present invention discloses a composite article having an electrically conducting surface, the process for making such a film with variable surface resistivity, and use of the invention as a flexible electric circuit element having both capacitance and resistance properties are described. Specific examples are given demonstrating the suitability of the media for use directly as passive RC filter networks with significant power dissipation potential. Additional examples demonstrate the suitability of the media for use as gas, vapor and liquid analyte sensors that derive sensing properties from the properties of the nanostructured composite film surface. The sensor functions uniquely in two distinct ways, first in terms of the dual mechanisms by which vapor/gas/liquid molecules affect sensor properties, and secondly with respect to the independent resistance and capacitance impedance properties that can be measured as a function of exposure to the vapor, gas, or liquid.

Figure 1:
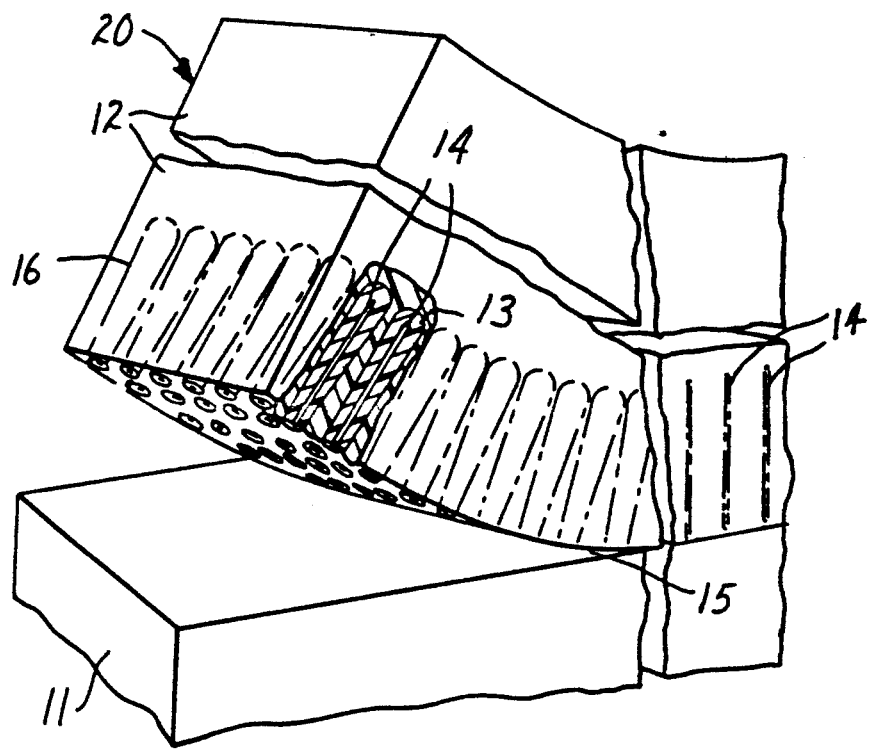
FIG. 1 illustrates a perspective view of an article with a nanostructured composite surface being delaminated from a substrate according to the present invention with a cut away portion showing the composite whisker-like structures.

Referring to FIG. 1, composite article 20 comprises encapsulant layer 12, for example, a polymer that has encapsulated in layer 12 arrayed microstructures 16, which may also be composites preferably initially oriented normal to the substrate 11. Each microstructure 16 comprises whisker-like structure 14 and optionally, conformal coating 13 enveloping whisker-like structure 14. The chemical composition of microstructures 16 is determined by the starting material deposited on substrate 11 to form the whisker-like structures 14 and the conformal coating 13 subsequently applied to the whisker-like structures 14. Microstructures 16 may be randomly or regularly arrayed in encapsulating layer 12.

As shown in FIG. 1, composite article 20 is partially delaminated from substrate 11 and delamination of composite article 20 is occurring at interface 15. Delamination of the composite article 20 from substrate 11 takes microstructures 16 along, embedded precisely in the surface of encapsulant layer 12 and exposes one cross-sectional end of each microstructure 16, wherein a surface of the encapsulating material of encapsulant layer 12 and the exposed cross-sectional ends of microstructures 16 are coincident on a common side. The topography of the delaminated surface, or exposed surface of the composite article 20 is the inverse of the topography of the surface of substrate 11 from which it is delaminated. Furthermore, the exposed surface of the composite article 20 is electrically reactive, that is, exhibits surface electronic phenomena, such as resistance and capacitance. If the surface of substrate 11 is perfectly smooth, the exposed cross-sectional ends of microstructures 16 and the delaminated surface of the encapsulating layer will be on a common plane.

The unique fracture and adhesion properties of whisker-like structures 14 at substrate interface 15 allow whisker-like structures 14 to withstand the coating and encapsulating processes, yet be easily and cleanly delaminated from substrate 11.

The thickness of conformal coating 13 applied to whisker-like structures 14, and intrinsic resistivity of said conformal coating 13, are the primary parameters controlling the surface electronic conductivity of composite article 20.

It should be noted that composite article 20 can have the conducting area formed into patterns suitable for building electronic circuits by several means. For example, starting material, for example, perylene pigment, can be deposited through a mask, or the conducting conformal coating can be applied to the whisker-like structures through a mask, or the encapsulant can be photolithographically applied to encapsulate the coated whisker-like structures image-wise. The small volume and flexibility of the medium of the present invention allows it to be used in a wide variety of resonant circuit constructions. Additionally, the exposed surface of the composite article, that is the reactive surface, can be coated in a patterned manner with an insulator or other dielectrics.

Materials useful as a substrate for the present invention include those which maintain their integrity at the temperatures and pressures imposed upon them during any deposition and annealing steps of subsequent materials applied to the substrate. The substrate may be flexible or rigid, planar or non-planar, convex, concave, aspheric or any combination thereof.

Preferred substrate materials include organic or inorganic materials, such as, polymers, metals, ceramics, glasses, semiconductors. Preferred organic substrates include polyimide film, commercially available under the trade designation KAPTON ™ from DuPont Corp., Wilmington, Del. Additional examples of substrate materials appropriate for the present invention can be found in U.S. Pat. No. 4,812,352 and is incorporated herein by reference.

Starting materials useful in preparing the whisker-like structures include organic and inorganic compounds. The whisker-like structures are essentially a non-reactive or passive matrix for the subsequent conformal coating and encapsulating material. In addition to starting materials that produce whisker-like structures, several techniques or methods are useful for producing the whisker-like configuration of the particles.

For example, methods for making organic microstructured layers are disclosed in *J Sci. Technol. A,* vol. 5, no. 4, July/August (1987), pgs 1914–16; *J. Sci. Technolol. A,* vol. 6, no. 3, May/June (1988), pgs 1907–11; *Thin Solid Films,* vol. 186, (1990), pgs 327–47; U.S. Pat. No. 3,969,545; *Rapid Quenched Metals,* (Proc. of the Fifth Int'l Conf. on Rapidly Quenched Metals), Wurzburg, Germany, Sept. 3–7 (1984); S. Steeb et al. Eds. Elsevier Science Publishers B.V., New York (1985), pgs 1117–24; U.S. Pat. No. 4,568,598; *Photo. Sci. and Eng.,* vol. 24, no. 4, July/August, (1980), pgs 211–16; and U.S. Pat. No. 4,340,276, the disclosures of which are incorporated herein by reference.

Methods for making inorganic-, metallic-, or semiconductor-based microstructured-layers or whisker-like structures are disclosed in U.S. Pat. No. 4,969,545; *J. Vac. Sci. Tech. A,* vol. 1, no. 3, July/Sept. (1983), pgs 1398–1402; U.S. Pat. No. 4,252,864; U.S. Pat. No. 4,396,643; U.S. Pat. No. 4,148,294; U.S. Pat. No. 4,155,781; and U.S. Pat No. 4,209,008, the disclosures of which are incorporated herein by reference.

The organic compounds include planar molecules comprising chains or rings over which $\pi$-electron density is extensively delocalized. These organic materials generally crystallize in a herringbone configuration. Preferred organic materials can be broadly classified as polynuclear aromatic hydrocarbons and heterocyclic aromatic compounds. Polynuclear aromatic hydrocarbons are described in Morrison and Boyd, *Organic Chemistry* 3rd ed., Allyn and Bacon, Inc. (Boston, 1974), Chap. 30. Heterocyclic aromatic compounds are described in Chap. 31 of the same reference.

Preferred polynuclear aromatic hydrocarbons include, for example, naphthalenes, phenanthrenes, perylenes, anthracenes, coronenes, and pyrenes. A preferred polynuclear aromatic hydrocarbon is N,N'-di(3,5-xylyl)perylene-3,4:9,10 bis(dicarboximide), commercially available under the trade designation of C. I. Pigment Red 149 (American Hoechst Corp., Sommerset, N.J.) [hereinafter referred to as perylene red].

Preferred heterocyclic aromatic compounds include, for example, phthalocyanines, porphyrins, carbazoles, purines, and pterins. More preferred heterocyclic aromatic compounds include, for example, porphyrin, and phthalocyanine, and their metal complexes, for example copper phthalocyanine. Such a compound is available, from Eastman Kodak, Rochester, N.Y.

The organic material for whisker-like structures may be coated onto a substrate using well-known techniques in the art for applying a layer of an organic material onto a substrate including but not limited to vacuum evaporation, sputter coating, chemical vapor deposition, spray coating, Langmuir-Blodgett, or blade coating. Preferably, the organic layer is applied by physical vacuum vapor deposition (i.e., sublimation of the organic material under an applied vacuum). The preferred temperature of the substrate during deposition is dependent on the organic material selected. For perylene red, a substrate temperature near room temperature (i.e., about 25° C.) is satisfactory.

In the preferred method for generating organic whisker-like structures, the thickness of the organic layer deposited will determine the major dimension of the microstructures which form during an annealing step. Whisker-like structures 14 are grown on a substrate 11 with the characteristics and process described in U.S. patent application Ser. No. 07/271,930, now U.S. Pat. No. 5,035,961, filed Nov. 14, 1988 and incorporated herein by reference. The process for obtaining whisker-like structures 14 is also described in Example 1 hereinbelow. Preferably, when the organic material is perylene red the thickness of the layer, prior to annealing is in the range from about 0.05 to about 0.25 micrometer, more preferably in the range of 0.05 to 0.15 micrometer. The organic materials are annealed and produce a whisker-like structure. Preferably, the whisker-like structures are monocrystalline or polycrystalline rather than amorphous. The properties, both chemical and physical, of the layer of whisker-like structures are anisotropic due to the crystalline nature and uniform orientation of the microstructures.

Typically, the orientation of the whisker-like structures is uniformly related to the substrate surface. The structures are preferably oriented normal to the substrate surface, that is, perpendicular to the substrate surface. Preferably, the major axes of the whisker-like structures are parallel to one another. The whisker-like structures are typically uniform in size and shape, and have uniform cross-sectional dimensions along their major axes. The preferred length of each structure is in the range of 0.1 to 2.5 micrometers, more preferably in the range of 0.5 to 1.5 micrometers. The diameter of each structure is preferably less than 0.1 micrometer.

Preferably, whisker-like structures 14, shown in FIG. 1, are substantially uniaxially oriented. Microstructures, 16, are a submicrometer in width and a few micrometers in length, and are composites comprising an organic pigment core whisker conformally coated with a conducting material.

The whisker-like structures preferably have a high aspect ratio, (i.e., a length to diameter ratio in the range from about 3:1 to about 100:1). The major dimension of each whisker-like structure is directly proportional to the thickness of the initially deposited organic layer. The areal number densities of the conformally coated microstructures 16 are preferably in the range of 40 to 50 per square micrometers.

The conformal coating material will generally strengthen the microstructures comprising the microstructured-layer. Preferably, the conformal coating material has electrically conductive properties and is selected from the group consisting of an organic material, such as electrical conducting organic materials, for example see "the Organic Solid State" Cowen et al., *Chem & Eng. News,* July 21 (1986) pgs 28–45, a metallic material, or a semiconductor inorganic material, such as silicon or gallium arsenide. More preferably, the conformal coating material is a metal or metal alloy. Preferably, the metallic conformal coating material is selected from the group consisting of aluminum, cobalt, nickel chromium, cobalt chromium, copper, platinum, silver, gold, iron, and nickel.

Preferably, the organic conformal coating material is selected from the group consisting of hetrocyclic polynuclear aromatics. The preferred inorganic conformal coating material is a semiconductor.

Preferably, the wall thickness of the conformal coating surrounding the whisker-like structure is in the from about 0.5 nanometers to about 30 nanometers.

The conformal coating may be deposited onto the microstructured-layer using conventional techniques, including, for example, those described in U.S. patent application Ser. No. 07/271,930, now U.S. Pat. No. 5,035,961, supra. Preferably, the conformal coating is deposited by a method that avoids the disturbance of the microstructured-layer by mechanical or mechanical-like forces. More preferably, the conformal coating is deposited by vacuum deposition methods, such as, vacuum sublimation, sputtering, vapor transport, and chemical vapor deposition.

Preferably, the encapsulating material is such that it can be applied to the exposed surface of the conformal-coated microstructured-layer in a liquid or liquid-like state, which can be solidified. The encapsulating material may be in a vapor or vapor-like state that can be applied to the exposed surface of the conformal-coated microstructured-layer. Alternatively, the encapsulating material is a solid or solid-like material, preferably powder or powder-like, which can be applied to the exposed surface of the conformal-coated microstructured-layer, transformed (e.g., by heating) to a liquid or liquid-like state (without adversely affecting the conformal-coated microstructured-layer composite), and then resolidified.

More preferably, the encapsulating material is an organic or inorganic material. The encapsulating material may exhibit sensitivity to gas or vapor contaminants to be detected. Additionally, it is preferable, although not required, that the encapsulant be permeable to gas or vapor contaminants.

Preferred organic encapsulating materials are molecular solids held together by van der Waals' forces, such as organic pigments, including perylene red, phthalocyanine and porphyrins and thermoplastic polymers and co-polymers and include, for example, polymers derived from olefins and other vinyl monomers, condensation polymers, such as polyesters, polyimides, polyamides, polyethers, polyurethanes, polyureas, and natural polymers and their derivatives such as, cellulose, cellulose nitrate, gelation, proteins, and rubber. Inorganic encapsulating materials that would be suitable, include for example, gels, sols, or semiconductor, or metal oxides applied by, for example, vacuum processes.

Preferably, the thickness of the coated encapsulating material is in the range from about 1 micrometer to about 100 micrometers, and more preferably in the range from about 6 micrometers to about 50 micrometers.

The encapsulating material may be applied to the conformal-coated microstructured-layer by means appropriate for the particular encapsulating material. For example, an encapsulating material in a liquid or liquid-like state may be applied to the exposed surface of the conformal-coated microstructured-layer by dip coating, vapor condensation, spray coating, roll coating, knife coating, or blade coating or any other coating method known to those skilled in the art. An encapsulating material may be applied in a vapor or vapor-like state by using conventional vapor deposition techniques including, for example, vacuum vapor deposition, chemical vapor deposition, or plasma vapor deposition.

An encapsulating material which is solid or solid-like may be applied to the exposed surface of the conformal-coated microstructured-layer liquified by applying a sufficient amount of energy, for example, by conduction or radiation heating to transform the solid or solid-like material to a liquid or liquid-like material, and then solidifying the liquid or liquid-like material.

The applied encapsulating material may be solidified by means appropriate to the particular material used. Such solidification means include, for example, curing or polymerizing techniques known in the art, including, for example, radiation, free radical, anionic, cationic, step growth process, or combinations thereof. Other solidification means include, for example, freezing and gelling.

After the polymer is cured, the resulting composite article 20 comprising a conformal-coated microstructured-layer and an encapsulating layer 12 is delaminated from the substrate 11 at the original substrate interface 15 (see FIG. 1) by mechanical means such as, for example, pulling the composite layer from the substrate, pulling the substrate from the composite layer, or both. In some instances, the composite layer may self-delaminate during solidification of the encapsulating material.

Capacitive properties of the composite article are determined by the dielectric constants of the encapsulating material, film thickness and planar area used. Intimate contact of the conductive particles with the surrounding encapsulant permits the full dielectric response of the encapsulant to be realized with only physical contact of a circuit lead to the conducting side of the composite, that is, without evaporation or sputter coating of a metal overlayer on the polymer surface as is usually necessary to bring a conductor into full electrical contact with a dielectric surface.

It is also a unique property of this medium's structural anisotropy that the complex impedance is anisotropic. That is, the impedance parallel to the surface of the composite film is predominantly resistive, while the impedance in the direction perpendicular to the surface is predominantly capacitive, being determined by the very large reactance of the much thicker encapsulant layer.

Figure 2A:
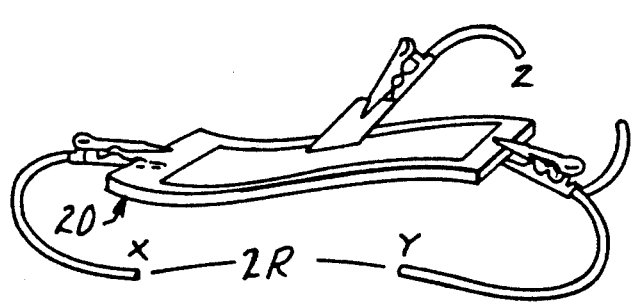
FIGS. 2 (a) and (b) illustrate a three terminal AC electric circuit configuration using metal foil tape as one contact to the invention and its simplified representative RC schematics.
Figure 2B:
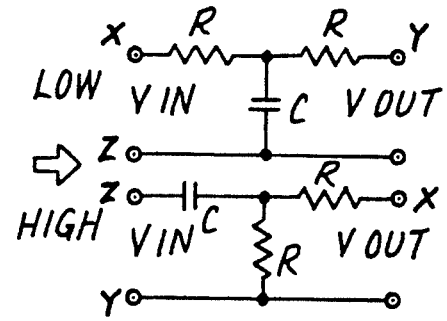

FIGS. 2 (a) and (b) illustrate a configuration utilizing the passive resistance (R) and capacitance (C) properties of thin flexible strips of the composite article of this invention. In all cases the resistance and capacitance character is spatially distributed over the entire area of the composite article. Referring to FIG. 2(a), a conductive metal foil tape is applied to the side of the encapsulating polymer opposite the conducting nanostructured side. Electrical contact can then be made at the three points x, y, and z. This is equivalent in a first order approximation to the three terminal network, as shown in FIG. 2(b). Depending on which pairs of terminals are used as input and output for an alternating current (AC) voltage signal, the composite strip can function as a low-pass or high-pass filter circuit. For example, applying the input signal across terminals x and z (or y and z) and taking the output across terminals y and z (or x and z) is equivalent to a low-pass filter. On the other hand, applying the input across terminals z and y (or z and x) and the output across terminals x and y (or y and x) produces a high-pass filter. Applying the output and input signals to the third combination of terminal pairs, for example, an input signal applied across terminals x and y (or y and x) and output measured across terminals z and y (or z and x), gives a simple capacitively coupled voltage divider. The metal foil tape need not be applied in a single piece and thus could produce multiple terminals. As used herein, "low-pass filter" means a filter network that passes all frequencies below a specified frequency with little or no loss. The term "high-pass filter" means a wave filter having a single transmission band extending from some critical frequency up to infinite frequency. The term "voltage divider" means a resistor or reactor connected across a voltage and tapped to make a fixed or variable fraction of the applied voltage available.

Figure 3A:
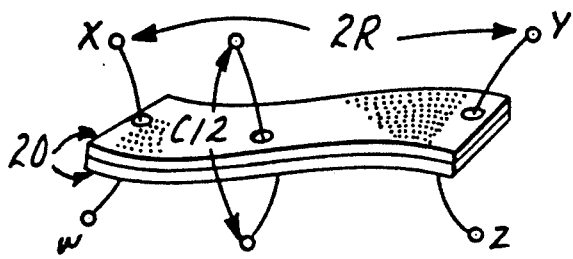
FIGS. 3 (a) and (b) illustrate two strips of nanostructured composite media, as shown in FIG. 1, adjacently positioned to form a four terminal network configuration and a simplified equivalent circuit.

FIGS. 3 (a) and (b) illustrate a configuration that forms a four terminal network with two pieces of the nanostructured composite film arranged in "parallel" such that the conductive sides of the composite film are facing outward and the corresponding equivalent electric circuit. Electrical contact is made at the ends of each side, illustrated as points w, x, y, and z as shown. This can similarly be utilized to have different filter characteristics depending on the various combinations of terminals used for input and output, or to form various two and three terminal networks.

FIGS. 4 (a) and (b) illustrate a configuration to form a four terminal network with two pieces of the composite film arranged in "series" and a simplified equivalent electrical circuit. This arrangement is approximately equivalent to a band pass filter. Electrical contact is made at the ends of each side at points w, x, y, and z as shown. The term "band pass filter" means a wave filter with a single transmission band, wherein the filter attenuates frequencies on either side of this band. The metal foil tape 22 can be replaced with other composite strips.

Referring again to FIG. 1, as a sensor, it is found that the in-plane surface resistivity of the nanostructured side of the composite article 20, the impedance to current flow in the plane of the whisker-like structures 14, is a simple yet sensitive probe of gas, vapor, or liquid analyte effects. The electrical conductance mechanism may involve both electron "percolation" from point-to-point where adjacent whiskers touch, and tunneling through or charge injection into the thin intermediate encapsulating material 12 interstitially located between the conductive conformal coated microstructures 16. Therefore, if the conductivity of this conformal coating 13 applied to the whisker-like structures 14, or the relative separation of the microstructures 16, or the charge transport properties of the intermediate encapsulating material 12 are affected by the analyte, the surface impedance of the composite article 20 is altered. The initial surface resistivity is easily varied over a wide range by controlling the thickness of the conductive conformal coating 13 applied to the whisker-like structure 14 prior to encapsulation.

Sensor medium is produced in a convenient flexible polymer form which may be cut into arbitrary sizes and shapes. Electrical connections are simply made by contact with the conducting, chemically active surface.

Referring to FIG. 1, again the physical structure of the composite article 20, utilized as a gas, liquid or vapor sensor, comprises a polymer film 12, optionally, sensitive to the vapor or gas of interest, having encapsulated in its surface a dense, random array of discrete whisker-like structures 14. The whisker-like structures 14 are typically about one to a few micrometers in length and submicrometer in width. Microstructures 16 comprise organic pigment core whisker-like structures 14 with a conformal coating 13, typically a conducting material, and optionally, sensitive to the vapor or gas to be sensed.

The structure of the composite medium is illustrated in FIG. 1 and described hereinabove. Preferably, the encapsulating material 12 and the conformal coating may be selected for sensitivity to the gas/vapor/liquid analyte see Katritzky et al., "New Sensor-Coatings for the Detection of Atmospheric Contamination and Water," supra. Gases, vapors or liquids typically sensed include but are not limited to acetone, methyl ethyl ketone, toluene, isopropyl alcohol, hydrogen sulfide, ammonia, carbon dioxide, carbon monoxide, nitrous oxide, sulfur dioxide, organophosphorus compounds in general, dimethyl methylphosphonate, chloroethyl ethyl sulfide, xylene, benzene, 1,1,1-trichloroethane, styrene, hexane, ethyl acetate, perchloro-ethylene, cyclohexane, VMP naphtha, cellosolves, chloroform, methylene chloride, Freon TM 113, ethanol, ethylene oxide, hydrogen fluoride, chlorine, hydrogen chloride, hydrogen cyanide, toluene diisocyanate, methylene di-p-phenylene isocyanate, and formaldehyde. The preferred sensing property of the sensor is the electrical impedance.

The sensing composite article of the present invention is a dual mode sensor since the conductive conformal coating and the polymer encapsulant may each be selected for their individual response to a particular analyte molecule of interest.

Figure 3B:
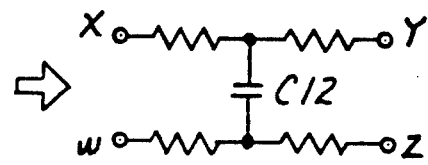

The sensing composite article is a dual sensor in a second aspect, as well. Constructing a sensor as illustrated in FIG. 3(b), the effect of vapor/gas molecules absorbed by the encapsulant on its dielectric properties can be sensed by changes in the capacitance being measured. Since this impedance in the perpendicular direction is predominantly determined by capacitance, and is unaffected by the in-plane resistivity of the whisker surface layer, the perpendicular-capacitance and in-plane resistance values are independent.

Since the microstructure's conformal coating and the encapsulant may independently be chosen to have varying degrees of sensitivity to an arbitrary specific gas, vapor or liquid analyte, it is possible to combine a variety of such individually comprised sensors into a multiplexed array, whereby the integrated response of the array as a whole to an unknown gas, vapor or liquid composition, could be used to determine the composition of the unknown gas, vapor or liquid, the relative fractions of the components making up the later, or for a single analyte, the absolute concentration.

EXAMPLES

Objects and advantages of this invention are further illustrated by the following examples, but the particular materials and amounts thereof recited in these examples, as well as other conditions and details, should not be construed to unduly limit this invention. Unless otherwise stated or apparent all materials used in the following examples are commercially available.

Examples 1 and 2 illustrate the basic procedure for preparing the composite articles of the present invention.

EXAMPLE 1

Organic pigment C.I. Pigment Red 149, (N,N'-di(3,5-xylyl)perylene-3,4:9,10-bis(dicarboximide)) [hereinafter referred to as perylene red], available from American Hoechst-Celenese, (Somerset, N.J.) was vacuum vapor deposited onto a stretched, 0.0125 mm thick sheet of copper coated polyimide, formed into a disc 8.3 cm in diameter. The resulting copper coated polyimide, having a 1000 Angstrom thick film of perylene red, was then annealed in vacuum, heating the entire continuous perylene red film coating the polyimide, by thermal conduction through the polyimide substrate. The perylene red film was heated at approximately 280° C. over a period of 90 minutes. After vacuum annealing, the disc had a nanostructured layer of discrete, oriented crystalline whiskers 1 to 2 μm in length. CoCr (86%/14%) was then sputter coated conformally onto the whiskers, using a conventional radio frequency (rf) glow discharge for 3 minutes at 13.7 MHz, with a 20 cm diameter target, 10 cm substrate-to-target distance, 24 mTorr of Argon (Ar), 500 watts of forward power and 1200 volts target bias.

Five milliliters (mL) of DUCO TM Cement "Household Cement" (Devcon Corporation), a solution of thermoplastic resin in toluene and other solvents, were applied to the center of the sample disc while spinning at 200 rpm. The disc was stopped when the cement flowed out to the perimeter of the sample disc. After air drying at room temperature for approximately 5 hours, the resulting nanostructured composite easily delaminated from the original polyimide substrate, producing a smooth surface where the now solidified cement had interfaced with the polyimide. The resulting dried thickness of the composite film was approximately 0.12 mm.

Two rectangular pieces of the composite were cut from different sections of the sample disc to give a sample with an area of 1.55 cm$^2$. The end-to-end resistance of one strip was measured to be 12,060 ohms and the second strip measured 2910 ohms. The strips were pressed together between glass microscope slides with the electrically conducting nanostructured surfaces facing outward. The sinewave output from a signal generator over the frequency range of 1 kHz to 10 MHz was applied across the conductive surfaces on one end of the composite strip, that is the terminals x and w shown in FIG. 3(a). The output signal developed across contacts y and z shown in FIG. 3(a) were monitored with an oscilloscope having a 1 megohm, 20 picofarad (pF) input impedance using a 1× probe, or with a 10× probe having a 10 megohm, 13 pF impedance.

Figure 5:
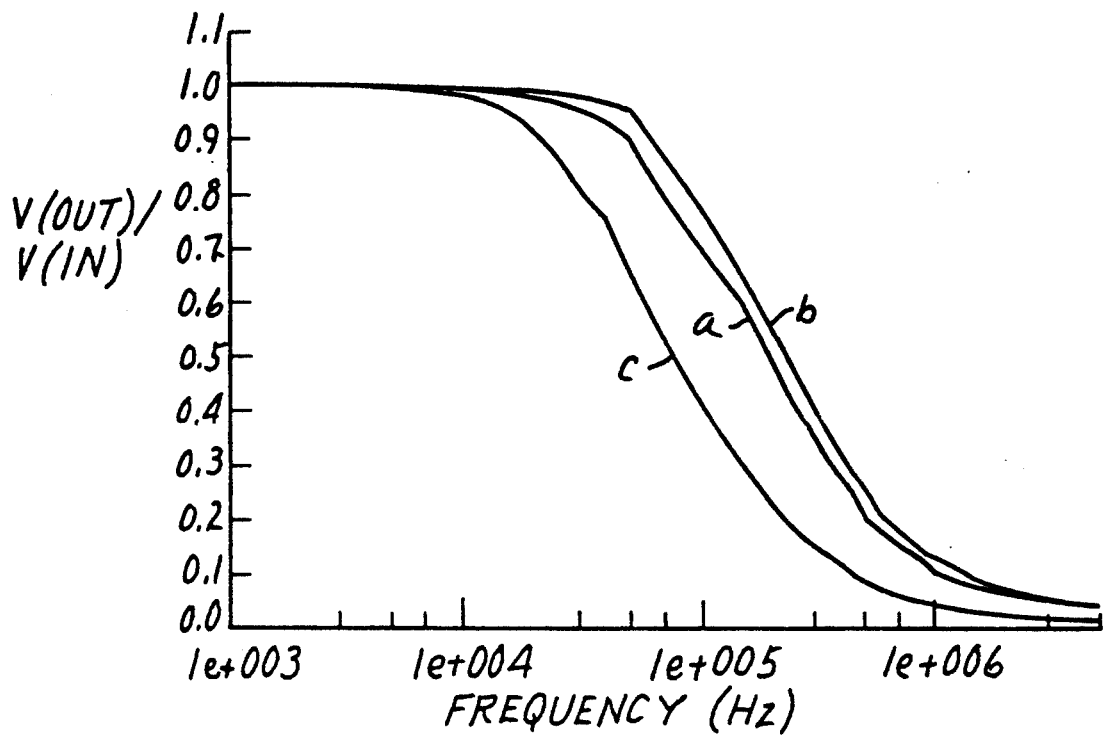
FIG. 5 is the graphic representation of the low-pass AC filter transfer function measured for Examples 1 and 2.

FIG. 5, curve (a) shows the measured output signal peak-to-peak amplitude normalized to that of the input signal. It is seen that the composite strips have an electronic transfer function similar to a low pass RC network, with a fall-off of approximately 6 dB/decade.

EXAMPLE 2

A second 8 cm diameter sample disc was prepared as described in Example 1, except CoCr was sputtered onto the perylene whiskers for 4 minutes at the conditions of Example 1, followed by encapsulation with 3 ml of DUCO TM cement. Two pairs of rectangular strips were cut from the sample and pressed together between glass microscope slides to form two composite strips. The same AC signal transfer function was measured as a function of frequency for each of these dual strips and are illustrated in FIG. 5. Referring to curve (b), the resistances of both sides of the dual composite strip (area of 2.7 cm$^2$) were approximately 4500 ohms. Referring to curve (c), the resistances were approximately 2200 ohms and area approximately 6.5 cm$^2$. The dual composite strip thicknesses were approximately 0.05 mm. The frequency "cut-off" values shift in response to the capacitance and resistance of the strips.

EXAMPLES 3-10

The following examples illustrate a range of nanostructured composite sample types, varying with respect to the coating on the perylene whiskers and the polymer encapsulant used, to generate a series of equivalent RC network circuits with low-pass and high-pass cut-off frequencies that vary over several orders of magnitude. All samples were identically prepared up to and including the growth of the perylene whiskers. In each example, the sample type was identified according to the composition listed in Table 1. In each case, Scotch TM brand aluminum foil backed adhesive tape (3M Co., St. Paul) was applied to the polymer encapsulant side of each sample piece. Electrical contact was then made to the ends of the sample strip on the nanostructured side, and the metal foil tape on the opposing side, to form the three terminal networks shown in FIG. 2. The resistance across the conducting side of each sample was measured with a Keithley model 617 digital electrometer. The capacitance of each sample was measured as described below. A conventional 1.025 megohm resistor was placed in series with terminal x of a sample capacitor (FIG. 2), and a squarewave signal in the 100 Hz to several kHz range was applied to the 1.025 megohm resistor and terminal z (FIG. 2) across the two circuit elements. The voltage signal decay across the sample terminals y and z was monitored with an oscilloscope (10× probe) and the RC time constant read directly from the sample's capacitance waveform, allowing C (capacitance) to be calculated from Equation I $$t = RC \tag{I}$$

where R is the resistance in ohms, C is the capacitance in farads and t is the decay time in seconds for capacitance to discharge to 1/e of the initial charge.

TABLE 1

| Sample Type | Conformal Coating | Encapsulant |
|---|---|---|
| A | Cu | DUCO TM Cement[1] |
| B | Cu | Urethane/Vinyl[2] |
| C | Cu | Fluorenone polyester[2] |
| D | Ag | DUCO TM Cement |
| E | Ag | Fluorenone polyester |
| F | Au | DUCO TM Cement |
| G | CoCr | DUCO TM Cement |
| H | CoCr | Fluorenone polyester |
| I | Au | Fluorenone polyester |

[1]Devcon Corp., Danvers, MA
[2]3M Co., St. Paul, MN

Figure 6:
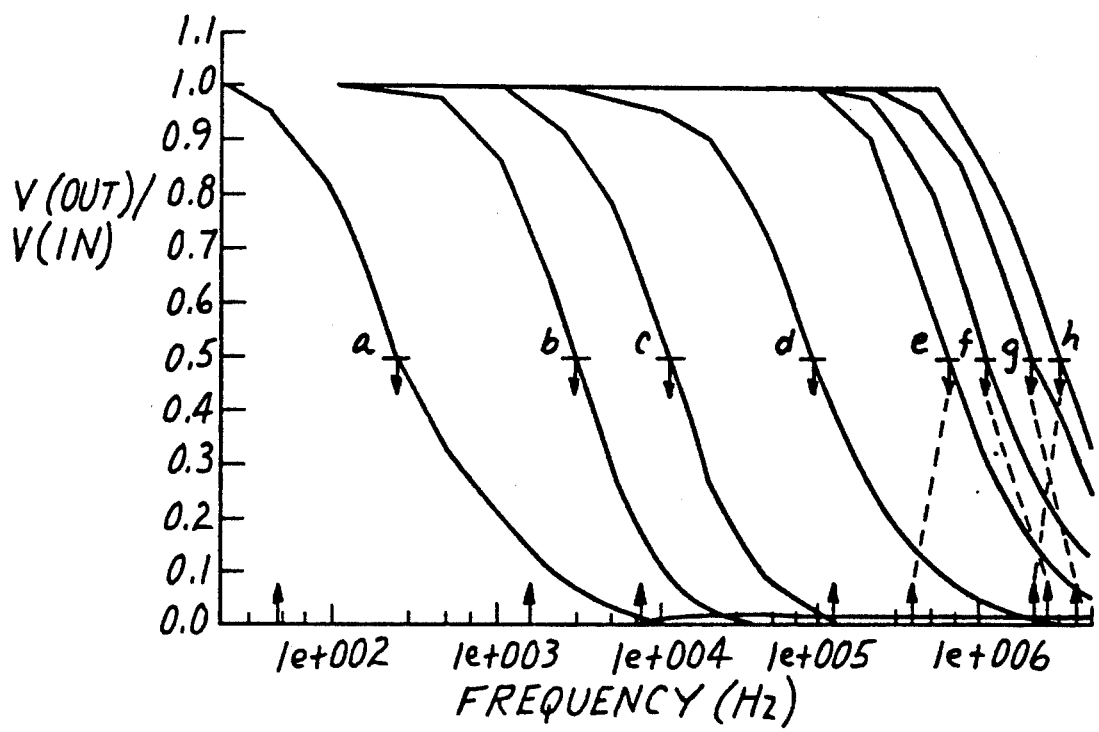
FIG. 6 is the graphic representation of the three terminal network low-pass frequency response functions for Examples 3 to 10.
Figure 7:
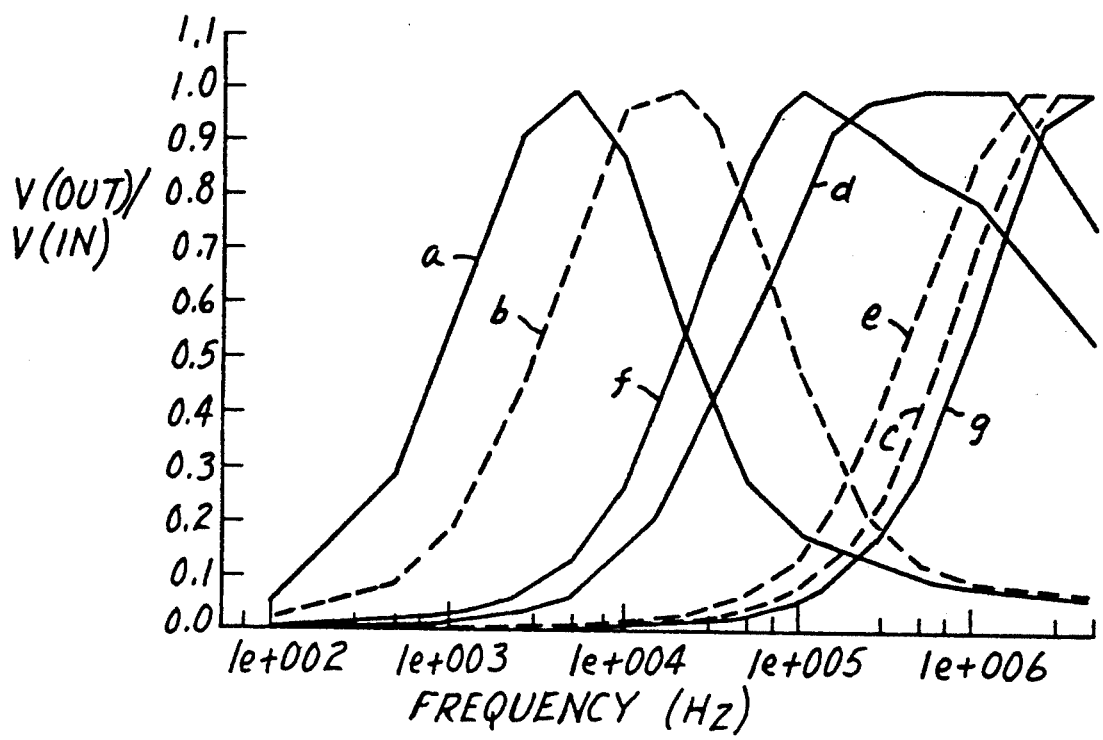
FIG. 7 is the graphic representation of the three terminal network high-pass frequency response function for Examples 3 to 10.

Examples 3-5 illustrate the passive network response of small flexible strips of type D samples. A type D oriented nanostructure was made by first evaporating 750 Angstroms (Å) mass equivalent of Ag onto perylene whiskers in a conventional diffusion pumped bell jar vacuum system operating at approximately 10$^{-6}$ Torr pressure range, and then encapsulating the nanostructure as described in Example 1. The sample parameters are shown in Table 2. The low-pass frequency response curves are shown in FIG. 6 and identified in Table 2. The high-pass frequency response curves are shown in FIG. 7 and identified in Table 2.

Examples 6-8 illustrate the passive RC network response of small flexible strips of type H samples. The type H oriented nanostructure was made by sputtering CoCr (5 minutes under the conditions of Example 1) onto perylene whiskers and encapsulating the nanostructure in fluorenone polyester (FPE) by spin coating 7 ml of a 5% solution in cyclohexanone at a revolution rate sufficient to just cover the entire 8 cm diameter sample disc, followed by air drying for 16 hours at room temperature and 4.5 hours at approximately 70° C. The sample parameters are shown in Table 2. The low-pass frequency response curves are shown in FIG. 6 and identified in Table 2. The high-pass frequency response curves are shown in FIG. 7 and identified in Table 2.

Example 9 illustrates the passive RC network response of a small flexible strip of type G sample. The oriented nanostructure was made by sputtering 750 Angstroms mass equivalent of CoCr onto the perylene whiskers and encapsulating them in 5 ml of DUCO TM cement as in Example 2. The sample parameters are shown in Table 2. The low-pass frequency response curves are shown in FIG. 6 and identified in Table 2. The high-pass frequency response curves are shown in FIG. 7 and identified in Table 2.

Example 10 illustrates the passive RC network response of a small flexible strip of type A sample. The oriented nanostructure was prepared by sputtering Cu to a mass equivalent of approximately 600 Å onto the perylene whiskers and encapsulating in DUCO TM cement. The results are shown in Table 2. The low-pass frequency response curves are shown in FIG. 6 and identified in Table 2. The high-pass frequency response curves are shown in FIG. 7 and identified in Table 2.

The response curves in FIG. 7 appear to be band pass frequency response curves rather than high-response curves. This is due to oscilloscope input impedance, which in combination with the sample strips' half resistances, act as a low pass filter following the high pass circuit configuration shown in FIG. 2(b).

conventional carbon resistor and a thin metal film coated polymer.

In Examples 11-18, thin strips of varying surface resistance, formed with various metal/polymer combinations as described in Table 1, were heated by passing current through the strip until the test strip failed. The strips were laid against a glass slide with the nanostructured side against the glass and a temperature probe pressed against the opposite polymer side of the strip to monitor the temperature rise as a function of current level. The glass slide was not cooled. The plots of temperature rise versus electrical power dissipated in the composite strips was observed to be linear. Table 3 summarizes the results of eight sample strips, made from five sample types, as described in Table 1. Table 3 summarizes $\Delta T/\Delta P$, the slope of the linear temperature versus power plot, the test strip resistance, area, thickness, volume, and the maximum current density at the time of failure. The current density is calculated assuming the current carrying layer of the strip is approximately 2 $\mu$m thick, which is the known thickness of the nanostructured region of the composite article.

The last entry of Table 3 identified as example 19, shows similar measurements from a standard 12 ohms, ¼ Watt carbon resistor, having cylindrical geometry. The current density of the carbon resistor is calculated using the inner carbon volume diameter. It is seen that the nanostructured composite films can support current densities 50 to 70 times larger than standard resistors of equivalent resistance and volume, for a similar tempera-

TABLE 2

| Example No. | Sample Type | Area (cm$^2$) | Thickness (mm) | Resistance (ohms) | Capacitance (pF) | Low-Pass Freq. Response (FIG. 6) | High-Pass Freq. Response (FIG. 7) |
|---|---|---|---|---|---|---|---|
| 3 | D | 12.1 | .04 | 26 × 10$^6$ | 146 | a | — |
| 4 | D | 1.54 | .04 | 1.86 × 10$^6$ | 61.5 | b | a |
| 5 | D | 3.52 | .04 | .20 × 10$^6$ | 96 | c | b |
| 6 | H | 2.37 | .025 | .023 × 10$^6$ | 63 | d | f |
| 7 | H | 13 | .02 | 1180–1290 | 425 | e | d |
| 8 | H | 3.9 | .02 | 560 | 171 | h | g |
| 9 | G | 2.5 | .07 | 1760 | 40 | f | e |
| 10 | A | 2.1 | .064 | 1005 | 51 | g | c |

EXAMPLES 11-19

In Examples 11-19, the power dissipation capability of the nanostructured composite article, used in purely a resistive mode, is demonstrated and compared to a ture rise. This is due in large part to the larger surface area for heat dissipation. For Examples 11-19, it can be shown that the thermal conductivity of the polymer forming the bulk of the strip is the limiting thermal dissipation factor.

TABLE 3

| Example No. | Sample Type | Area (cm$^2$) | Thickness (mm) | Volume (cm$^3$) | Resistance (ohms) | $\Delta T/\Delta P$ (°C./Watt) | J$_{MAX}$ (amps/cm$^2$) |
|---|---|---|---|---|---|---|---|
| 11 | F | 3.4 | .064 | .022 | 7.9 | 44.3 | 1412 ($\Delta T = 20°$ C.) |
| 12 | D | 3.0 | .066 | .020 | 12.7 | 29.0 | 1220 ($\Delta T = 16°$ C.) |
| 13 | D | 3.2 | .066 | .020 | 16 | 38.5 | 1061 ($\Delta T = 19°$ C.) |
| 14 | B | 3.6 | .025 | .009 | 33 | 23.0 | 375 ($\Delta T = 6.6°$ C.) |
| 15 | C | 1.2 | .051 | .0063 | 409 | 23.1 | 438 ($\Delta T = 25°$ C.) |
| 16 | D | 1.35 | .038 | .0051 | 1079 | 35.4 | 857 ($\Delta T = 15°$ C.) |
| 17 | C | 2.0 | .028 | .0056 | 5250 | 24.1 | 600 ($\Delta T = 7.9°$ C.) |
| 18 | G | 2.1 | .097 | .020 | 17730 | 27.3 | 225 ($\Delta T = 33°$ C.) |
| 19 | Std. Resistor | NA | NA | .030 | 12.2 | 40.2 | 19 ($\Delta T = 20°$ C.) |

EXAMPLES 20-23

In Examples 20-22, sample strips similar to those described in Examples 11-18 were resistively heated while heat-sinked to maximize the total power dissipation, and compared to Example 23, a cobalt film sputter-deposited on 0.05 mm thick polyimide. The sample strips were pressed tightly against a water cooled copper block with a thin film of heat transfer grease applied between the block and the polymer side of the nanostructured composite strips. Nextel TM (3M Co., St. Paul) insulating material was pressed against the nanostructured side of the strip, and a 0.025 mm diameter chromel-alumel (Type K) thermocouple measured the temperature at the midpoint of the conducting side of the strip through a small hole in the Nextel TM sheet. In this configuration, the surface temperature of the strip's conducting side was measured as a function of the input power, with thermal conductivity determined by the composite strip's polymer and its thickness, or in the case of the comparative Example 23, the polyimide substrate. The heat transfer grease, applied extremely thin, was observed to have a significant effect. The bulk thermal conductivity, k, across the thickness, d, of the polymer strip is simply related to the temperature drop across the strip, $\Delta T$, the planar area of the strip, A, the electrical power dissipated in the strip, P, as shown in Equation II.

$$k = \frac{Pd}{A\Delta T} \qquad (II)$$

The thermal conductivity was found typically to be on the order of 2 mWatts/cm$^{2\circ}$ C., indicative of a solid, polymer material.

Figure 8:
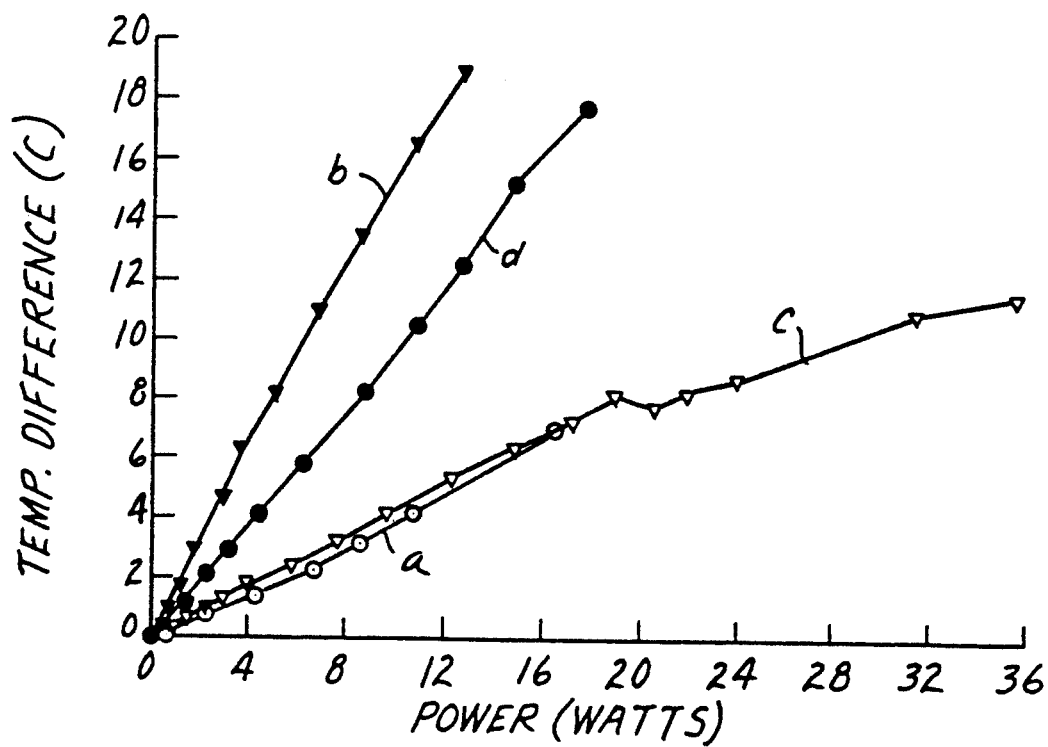
FIG. 8 is the graphic representation of the temperature rise of the nanostructured surface versus electrical power dissipated by the conducting layer of the composite media of Examples 20–23 of the present invention when the composite layer is heat-sinked (a to c), compared to a Co film sputtered onto polyimide.

For Example 20, composite article was formed by evaporating gold to a mass equivalent thickness of 1500 Angstroms onto an 8 cm diameter disc of perylene whisker coated polyimide, and encapsulating the latter with 6 ml of 4% solids FPE in cyclohexanone to form the nanostructured surface composite (type I) as described in Table 1. A test strip with an area of 4.0 cm$^2$, thickness of 0.005 mm and an end-to-end resistance of 10.8 ohms was placed on the Cu block assembly described above. Curve (a) in FIG. 8 shows the measured temperature difference across the strip versus power until failure of the strip occurred.

For Example 21, a surface composite of type E (see Table 1) was formed by evaporating 1500 Angstroms of Ag onto the whiskers and encapsulating with 10 ml of 4% FPE. A strip with an area of 4.0 cm$^2$, 0.05 mm thickness and 2.9 ohms resistance was mounted on the Cu block assembly. Curve (b) in FIG. 8 shows the measured temperature difference across the test strip versus the power dissipated in the strip.

For Example 22, a surface composite of type E was formed by evaporating 1950 Angstroms of Ag onto the whiskers and encapsulating with 10 ml of 4% FPE. A test strip with an area of 4.9 cm$^2$, thickness 0.014 mm and resistance of 2.2 ohms was placed on the Cu block assembly. Curve (c) of FIG. 8 shows the measured temperature difference across the strip versus the power dissipated in the strip.

For comparative Example 23, approximately 1250 Angstroms of cobalt was sputter deposited onto a 0.05 mm thick polyimide web, using the conditions of Example 1. A strip was cut with an area of 4.4 cm$^2$, and an end-to-end resistance of 2.8 ohms. Curve (d) in FIG. 8 shows the temperature difference across the polyimide strip versus the power input until failure, measured in same way as for Examples 20-22.

EXAMPLE 24

This example shows the use of the nanostructured composite film, with a metal coating and a polymer encapsulant, as a sensor capable of reversibly responding to a saturated vapor of acetone with a rapid response time and a sensitivity, according to Equation III $$S = (R - R_o)/R_o = 10\% \qquad (III)$$

The organic pigment C.I. Pigment Red 149, (N,N'-di(3,5-xylyl) perylene-3,4:9,10 bis(dicarboximide), (available from American Hoechst-Celenese), was vacuum vapor deposited onto a stretched, 0.05 mm thick sheet of copper coated polyimide, formed into a disc with a diameter of 8.3 cm. The disc was vacuum annealed to form a nanostructured layer of discrete, oriented crystalline whiskers approximately 1.5 micrometers tall, as described in Example 1. CoCr (86%/14%) was then sputter coated conformally onto the whiskers, using a conventional rf glow discharge at 13.7 MHz for 8 minutes with 20 cm diameter targets, 10 cm substrate-to-target distance, 24 mTorr of Ar, 500 Watts forward power, 1200 volts target bias and water cooling of the target and substrate.

Three milliliters of uncured photopolymer, (cyclohexyl methacrylate, hexamethylene diisocyanate trimethylolpropane 5 (CHMA, HMDI-TA5)), as prepared in U.S. Pat. No. 4,785,064 was applied to the center of the polyimide disc and hand tilted to cause the solution to uniformly flow over and encapsulate the CoCr coated perylene whiskers. The photopolymer was then cured by exposing it to the appropriate UV lamps, under N$_2$, for one-half hour.

The resulting nanostructured composite easily delaminated from the original polyimide substrate, (FIG. 1) producing a smooth, reflective surface where the now solidified polymer encapsulant had interfaced with the polyimide. An irregularly shaped piece of the brittle composite, approximately 5 cm long, 1.25 cm wide at the center and 0.5 cm wide at each end, was broken from the original disc. Electrical leads were attached to the ends by crimping on tinned solder lugs and coating them with conductive paint. The total resistance of the sample piece as described, was 843 ohms.

With leads from a Keithley model 616 electrometer attached to measure the resistance, and the latter driving a time based chart recorder, the sample was placed inside a covered 400 ml polyethylene beaker. With only air in the beaker, the resistance remained constant at 840 ohms for approximately 40 minutes. Acetone was then added to the covered beaker to a depth of 3 mm, so as to expose the sensor to a saturated vapor. The resistance (R) began to increase and rose to 855 ohms over a two minute interval. For approximately 15 minutes, the R remained at 855 ohms and then R increased sharply again to approximately 875 ohms over a period of 30 seconds and remained constant for 12 minutes. R then jumped to 900 ohms in a period of two minutes, thereafter remaining in the range of 900 to 880 ohms for 70 minutes. At this point, the sensor assembly was removed from the beaker and laid on the laboratory bench, whereupon R began dropping within seconds, reaching 790 ohms in 7 minutes and staying constant for 12 minutes until put back into the acetone vapor. R immediately began increasing again, reaching 900 ohms in 9 minutes where it remained constant.

In summary, this example of a nanostructured composite sensor with CoCr conformal coating and CHMA, HMDI-TA5 encapsulant has demonstrated the capability to rapidly and reversibly sense a room temperature saturated vapor of acetone with a sensitivity of approximately 10%.

The following example classes demonstrate the utility of the nanostructured composite film as gas/vapor sensors for $H_2S$, Hg vapor, $H_2O$ and organic vapors of methyl ethyl ketone (MEK), acetone, toluene, isopropyl and ethyl alcohol, and as a liquid analyte sensor for aqueous Br. In all cases basic whisker structured perylene films deposited on copper coated polyimide sheets such as described in Example 24 were used as the starting point, and various combinations of metal conformal coatings and polymer encapsulants used to form thirteen different types of nanostructured composite films. Table 4 lists these different samples according to metal coating and polymer encapsulant as types A-M, which are referenced for brevity in the following Examples.

Photopolymer A was prepared as described in U.S. Pat. No. 4,510,593, Examples 6 and 2 and is incorporated herein by reference.

Photopolymer B is a radiation-curable composition prepared as described in U.S. Pat. No. 4,986,496, Example 4 and is incorporated herein by reference.

| Components | Parts |
| --- | --- |
| urethane acrylate oligomer (XP51-85 TM, Cargile, Inc.) | 68 |
| tetraethylene glycol diacrylate (SR-268 TM, Sartomer, Co.) | 19 |
| diethoxyacetonphenone (DEAP TM, Upjohn Co.) | 5 |
| fluorochemical surfactant (FC-431 TM, 3M Co.) | 2.5 |
| n-vinyl pyrrolidone (GAF, Inc.) | 5 |
| UV light stabilizer (TINUVIN 770 TM, Ciba Geigy, Inc.) | 0.5 |

TABLE 4

| Sample Type | Conformal Coating | Encapsulant |
| --- | --- | --- |
| A | Ag | Photopolymer A[1] |
| B | Ag | DUCO TM Cement[2] |
| C | Ag | Photopolymer B[3] |
| D | Ag | Vinol polyvinyl alcohol |
| E | Cu | Fluorenone polyester[4] |
| F | Au | UV optical adhesive[5] |
| G | Au | DUCO TM Cement |
| H | CoCr | Photopolymer CHMA, HMDI-TA5[6] |
| I | CoCr | Photopolymer A |
| J | CoCr | Fluorenone polyester |
| K | Fe | DUCO TM Cement |
| L | Cu | DUCO TM Cement |
| M | CoCr | DUCO TM Cement |

[1] U.S. Pat. No. 4,510,593
[2] Devcon Corp., Danvers, MA
[3] U.S. Pat. No. 4,986,496
[4] 3M Co., St. Paul, MN
[5] Norland Products, Inc., New Brunswick, NJ
[6] U.S. Pat. No. 4,785,064 (cyclohexyl methacrylate, hexamethylene diisocyanate trimethylolpropane 5)

EXAMPLES 25-33

These examples demonstrate the utility of samples of types A, B, C, D, and E as irreversible sensors or dosimeters for $H_2S$ gas under conditions of high humidity, and illustrate the dependence of sensor sensitivity on the initial resistivity for quantitative analyses.

Example 25 illustrates that type B samples produce a significant response to $H_2S/N_2$ concentrations as low as 30 ppm in times as short as 30 seconds under conditions of 50% relative humidity (R.H.) and 30 l/min flow rates.

A strip of type B sample, made by evaporating 900 Angstroms mass equivalent of Ag and encapsulating to a thickness of 0.045 mm, was cut 6 mm wide and 4.5 cm long. Electrical contact to the strip was made by simply clipping smooth-jawed miniature alligator clips to the ends of the strip. The initial resistance was 870 ohms. The strip was supported within a sealed 9 oz. glass jar and the resistance continuously monitored while gas mixtures of known composition and flow rate were admitted and allowed to vent through tubes penetrating the jar cover. Two sources of gases were mixed in a preliminary 9 oz. jar that supplied the final mixed gas to the sample containing jar. The first gas source was wet $N_2$, produced by flowing $N_2$ over a humidistat (General Eastern) controlled water vapor bath through a glass flow meter tube (LabCrest No. 450–688).

Figure 9A:
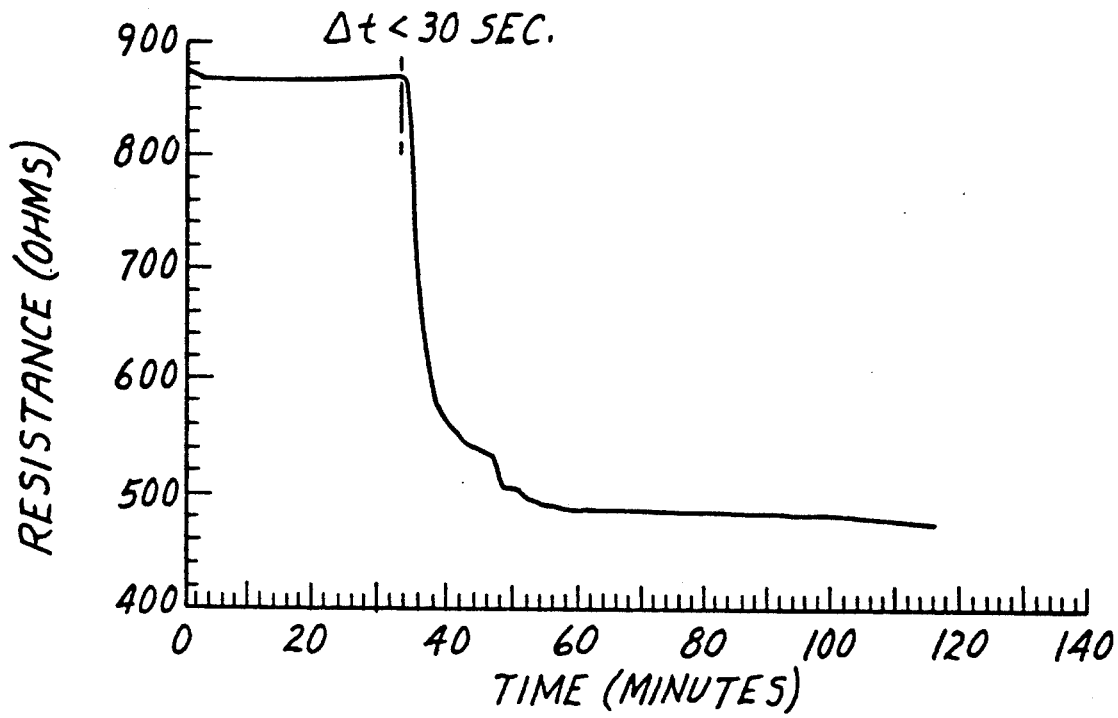
FIGS. 9 (a) and (b) is the graphic representation of the resistance change of type B sample of Examples 24 and 31.
Figure 9B:
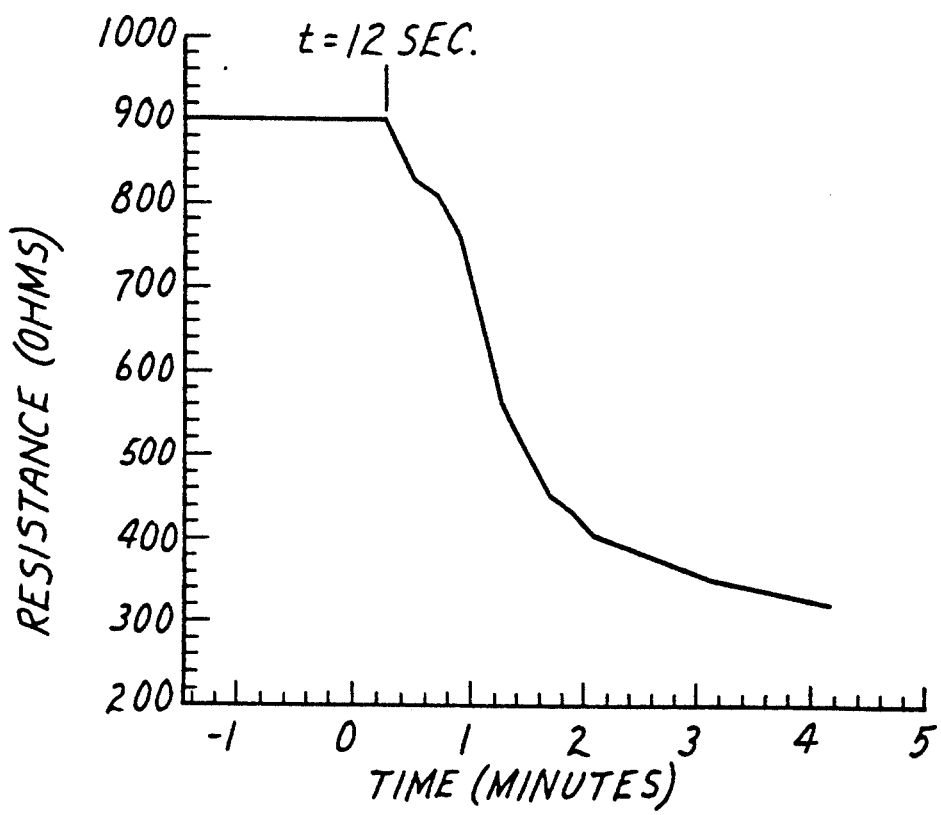

The second gas source was either pure $N_2$ or 108 ppm $H_2S/N_2$ (Union Carbide Industrial Gases Inc.) supplied to the mixing jar via a flow meter (Ace Glass Inc., tube #35). While flowing only humidified $N_2$ into the sample jar, the resistance remained constant at 869 ohms over a period of 35 minutes during which time the relative humidity was inceased from 50% to 78% in the first gas source, flowing at 16 l/min., and the second gas source of dry $N_2$ flowed at approximately 14 l/min., to produce a total flow of approximately 30 l/min. of humidified $N_2$ at approximately 25% to 39% RH. This demonstrates that a type B sensor is unaffected by water vapor, such as would exist in the vicinity of human breath. The valving of the second gas source was quickly switched to admit the 108 ppm $H_2S$ at approximately 5 l/min. in place of the dry $N_2$, and immediately the resistance began rapidly dropping at a rate exceeding 100 ohms/min. as shown in FIG. 9 (a), finally approaching a stable and nonreversible resistance of 490 ohms, a decrease of 44%. This represents an average relative resistance change of 11%/min. over the first two minutes. The relative flow rates and mixture values imply that the rapid and large response of the strip's resistance was produced by approximately 30 ppm $H_2S/N_2$ at approximately 40% RH.

For Example 26, a second strip of type B sample, 4.5 cm ×5 mm, having a lower resistivity than Example 25, was mounted in the same test apparatus as Example 25. The initial resistance of the strip was constant at 130.7 ohms while exposed to the wet $N_2$ gas mixture flowing into the mixing jar at approximately 23 l/min. and 55% RH. Upon switching to a mixture containing 35 ppm $H_2S$ gas, the resistance began dropping within seconds, reaching approximately 105 ohms in 2 minutes and eventually 82.2 ohms after 20 minutes. This represents an average relative change of resistance of approximately 10%/min. over the first two minutes, similar to Example 25, despite the difference in initial resistivity. It should be noted that the very stable resistance to nearly 1 part per thousand implies that even just a 25 ohms change from 130 ohms is still a signal to noise ratio of 20%/0.1% or 200/1.

For Example 27, a third strip of type B sample used in Examples 25 and 26 had an initial resistance of 3900 ohms. Unlike the previous examples, some sensitivity to water vapor was noted. The strip was mounted in the same test apparatus, but a simpler gas admission system was used in which either dry $N_2$ or the 108 ppm $H_2S//N_2$ gas mixture could be admitted directly to the jar and vented through a second tube in the jar cover. Two ml of distilled water was added to the bottom of the test apparatus. The flow rates were not quantified, but produced a fast bubble out the 3 mm diameter (O.D.) vent tube when its outer end was placed in water. Upon switching from the pure $N_2$ to the $H_2S/N_2$ gas, the sample resistance increased briefly to 4150 ohms over 30 seconds, then plummeted to 1000 ohms in 90 seconds, a sensitivity of 50%/min, and reached 260 ohms after 6 minutes. In comparison to the previous examples, this example indicates that the nanostructured composite sensitivity to $H_2S$ may be correlated to the initial resistivity.

For Example 28, a similar strip of type B sample, with 1000 Angstroms mass equivalent Ag, and a very low initial resistance of 15.4 ohms, was exposed to the same gas flow conditions as used in Examples 25 and 26. No response to the $H_2S$ gas was noted after switching from wet $N_2$. This comparative example to Examples 25 to 27 indicates that too low an initial resistivity is not desirable. Sensitivity may be correlated to initial resistivity, probably because a different conduction mechanism may be dominating the current flow which is less sensitive to initial small degrees of reaction with the $H_2S$.

For Example 29, a strip of type D sample, made by annealing the perylene whiskers at 240° C. for 80 minutes, vacuum evaporating 1000 Angstroms mass equivalent of Ag onto the whiskers, and solution coating with a 5% solution of vinol-polyvinyl alcohol in water with 0.1% Triton X-100, (Rohm & Haas, Philadelphia, Pa.) was cut 5 cm long and 6 mm wide. The strip's initial resistance under flowing dry $N_2$ in the simpler gas flow arrangement of Example 27 was 34 ohms. Switching to the 108 ppm $H_2S/N_2$ gas source, in the absence of any water vapor in the apparatus produced no change in resistance. Three milliliters of water were added to the apparatus and the gas flow sequence repeated. With water vapor present, the resistance began dropping 90 seconds after switching to the $H_2S$ and exhibited a relative resistance drop of 10% over a period of approximately 11 minutes. This degree of change is also qualitatively consistent for such a low initial resistivity and the observations of the previous examples. It also indicates with this polymer encapsulant the need for finite relative humidity.

Figure 10:
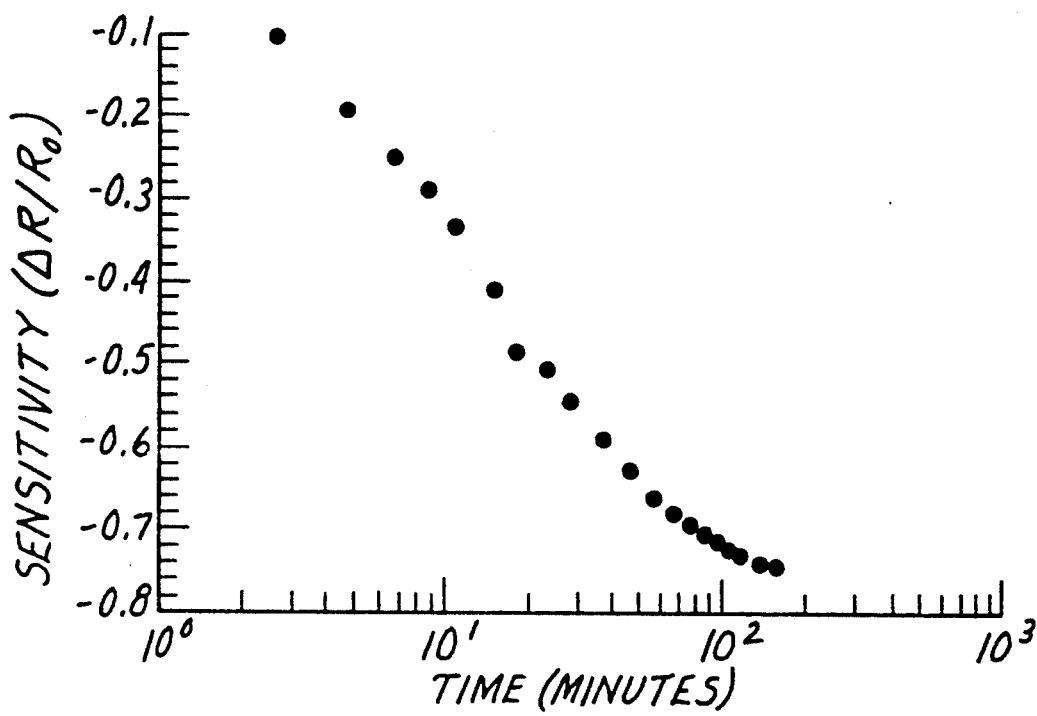
FIG. 10 is the graphic representation of the sensitivity versus exposure time for type C samples of Example 30.

For Example 30, a strip of type C sample, made by annealing the perylene at 280° C. for 90 minutes, vacuum evaporating 1035 Angstroms mass equivalent of Ag and spin coating 3 ml of photopolymer B onto an 8 cm diameter disc and UV curing, was cut 3.7 cm long and 6 mm wide. The strip was exposed to $N_2$ and a 108 ppm $H_2S/N_2$ gas mixture in the simpler gas flow arrangement of Example 27. Distilled water was present in the bottom of the apparatus. The initial resistance of the strip was 1.36K ohms and remained constant in a pure $N_2$ flow. Switching to the 108 ppm $H_2S/N_2$ flow, the resistance began dropping after 1.0 minute, and decreased logarithmically as shown in FIG. 10.

For Example 31, a strip of type B sample with an initial resistance of 898 ohms was placed in the simpler gas flow arrangement of Example 27. Distilled water was present in the bottom of the apparatus. With only pure $N_2$ flowing into the apparatus, adequate to produce a fast bubble from the outlet tube, the resistance was constant. Upon switching to the 108 ppm $H_2S/N_2$ flow, the resistance versus time curve broke at $t=12$ seconds after the start of the $H_2S$ flow, as shown in FIG. 9 (b), dropping at an initial rate of 36%/min, reaching less than 400 ohms within two minutes.

Example 32 shows that the resistance can also increase due to $H_2S$ exposure with a different metal coating on the whiskers and polymer encapsulant.

Figure 11:
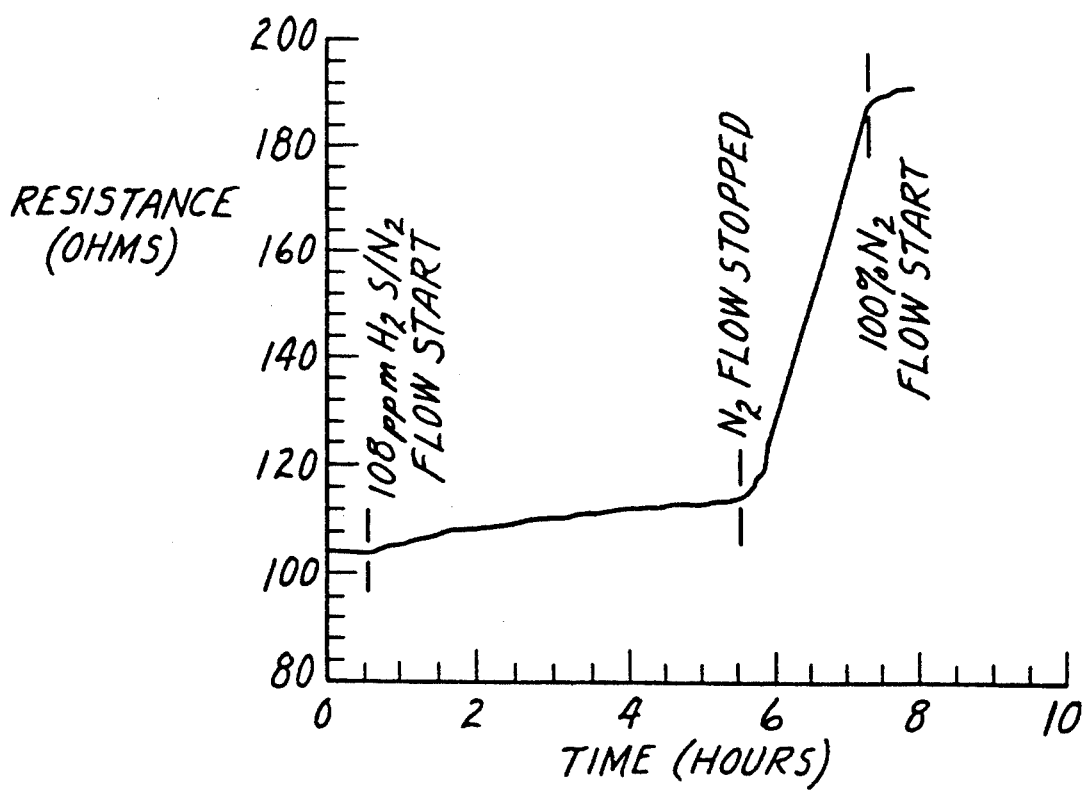
FIG. 11 is the graphic representation of the resistance change versus time for type E samples of Example 32.

An example of type E was prepared by annealing the perylene whiskers for 160 minutes and sputter coating Cu for two minutes under the same rf and Ar pressure as cited in Example 24. It was then encapsulated in fluorenone polyester (FPE) by spin coating 5 ml of a 5% solution of FPE in cyclohexanone at a rate of 170 rpm onto an 8 cm diameter disc sample. After air drying, the FPE encapsulated nanostructured composite was cleanly delaminated from the original copper coated polyimide substrate. A piece with an initial resistance of 104 ohms was cut and mounted in the simpler gas flow arrangement described in Example 27. There was no water vapor present. Upon switching from pure $N_2$ to the 108 ppm $H_2S/N_2$ flow the resistance began increasing very slowly as shown in FIG. 11. After several hours the resistance had increased to only 113.7 ohms, at which point the flow was stopped and the remnant vapors left in the sealed apparatus. As indicated in FIG. 11 the resistance began changing much more rapidly during the static conditions, until the pure $N_2$ flow was restarted.

In contrast to Examples 25 to 31, Example 33 illustrates that the resistance can increase upon $H_2S$ exposure even if Ag is used to coat the whiskers but a different encapsulant is used.

A type A sample was prepared by vapor coating a whiskered perylene sample with approximately 800 Angstroms of Ag, spin coating 5 ml of the ORP photopolymer at 450 rpm onto an 8 cm diameter sample disc, and UV curing. A piece with an initial resistance of 40.8 ohms was mounted in the simpler gas flow arrangement of Example 27. Distilled water was present in the bottom of the apparatus. With pure $N_2$ flowing, the resistance was constant to within 0.1 ohm. Upon switching to the 108 ppm/$N_2$ flow, the resistance began changing within 30 seconds, dipped briefly to 40.0 ohms over 2 minutes, and then began increasing monotonically, ultimately reaching 54.5 ohms after approximately 90 minutes. As in Example 32, it was observed that under static conditions, the rate of resistance change was faster than with positive flow. This effect is interpreted as due to nonequilibrium gas mixing in the simple single jar flow arrangement described in Example 27, and lowering of the relative humidity in the jar when the dry gas mixture is admitted.

In summary, Examples 25 to 33 show that the polymer encapsulant and metal coating both contribute to the response of the sensor to $H_2S$, even causing the resistance to change in opposite directions for different combinations of metal and encapsulant, providing evidence that the conduction mechanisms and gas sensitivity involve both constituents of the nanostructure, unlike the prior art. These examples also show that a particularly useful combination for a fast, sensitive $H_2S$ sensor, which is not affected by humid air alone is Ag and DUCO ™ cement.

Figure 17:
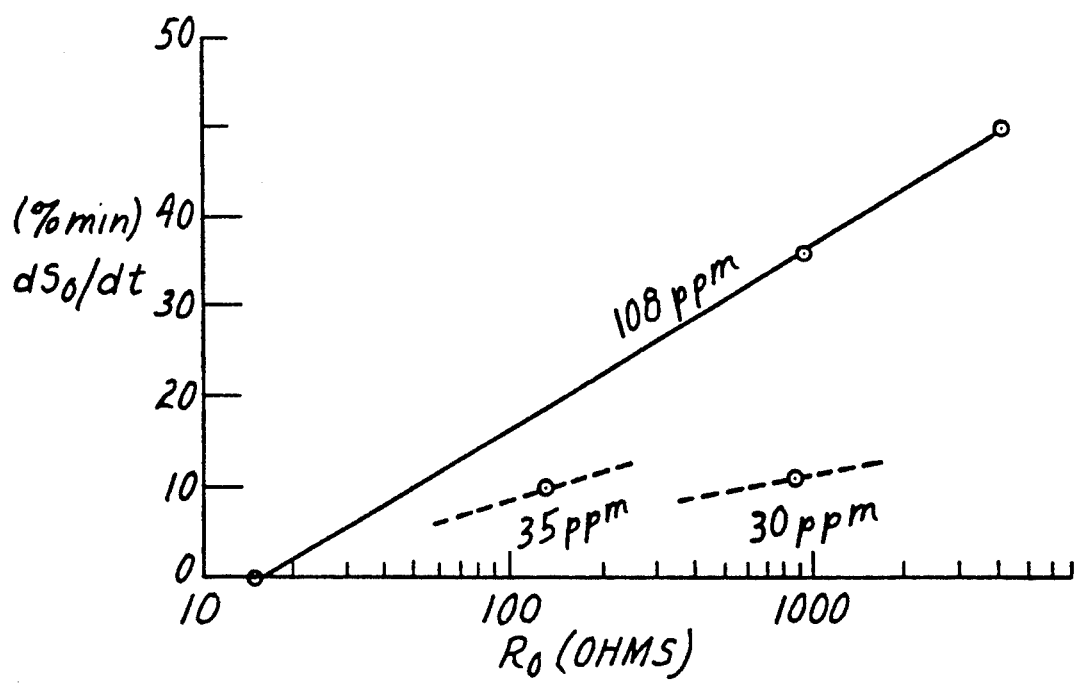
FIG. 17 is a graphic representation of the linear relationship of the sensor resistance changes versus the log of the initial resistivity, wherein the slope is ostensibly proportional to the analyte concentration.

Specifically for this combination and 108 ppm $H_2S/N_2$, Examples 27, 28 and 31 illustrate a logarithmic dependence of the initial rate of relative resistance change, $1/R_o(dR_o/dt)$, (or $dS_o/dt$ in %/min), on initial resistance, $R_o$, as shown in FIG. 17. This result is potentially very important since it indicates a simple means to quantify the analyte concentration with these sensors. It is logical to assume that the slope of the straight line in FIG. 17 will vary with the relative concentration of $H_2S$, and in fact this is supported by Examples 25 and 26 where effective concentrations of 30 and 35 ppm respectively produced initial sensitivity rates of approximately 10%/min for initial resistances of 870 and 131 ohms respectively. These data points are shown in FIG. 17 with dashed lines to indicate the hypothetical slope at those concentrations. (Note that all samples are type B samples). Given then two or more sensors, of different initial resistance, responding to the same gas concentration, it is only necessary to measure the initial rate of resistance change for each sensor, over one to two minutes, calculate the slope of a plot of the initial resistance rate of change versus resistance as indicated in FIG. 17, and compare to a calibration table to determine the analyte concentration. All of this could be done via integrated circuitry, and a multiplexed array of several of these sensors of regularly varying resistance could perhaps give good accuracy as well.

EXAMPLES 34 and 35

Examples 34 and 35 show that using gold as the conformal coating on the whiskers produces a mercury vapor sensor with a reaction mechanism dominated by solid state diffusion.

Figure 12:
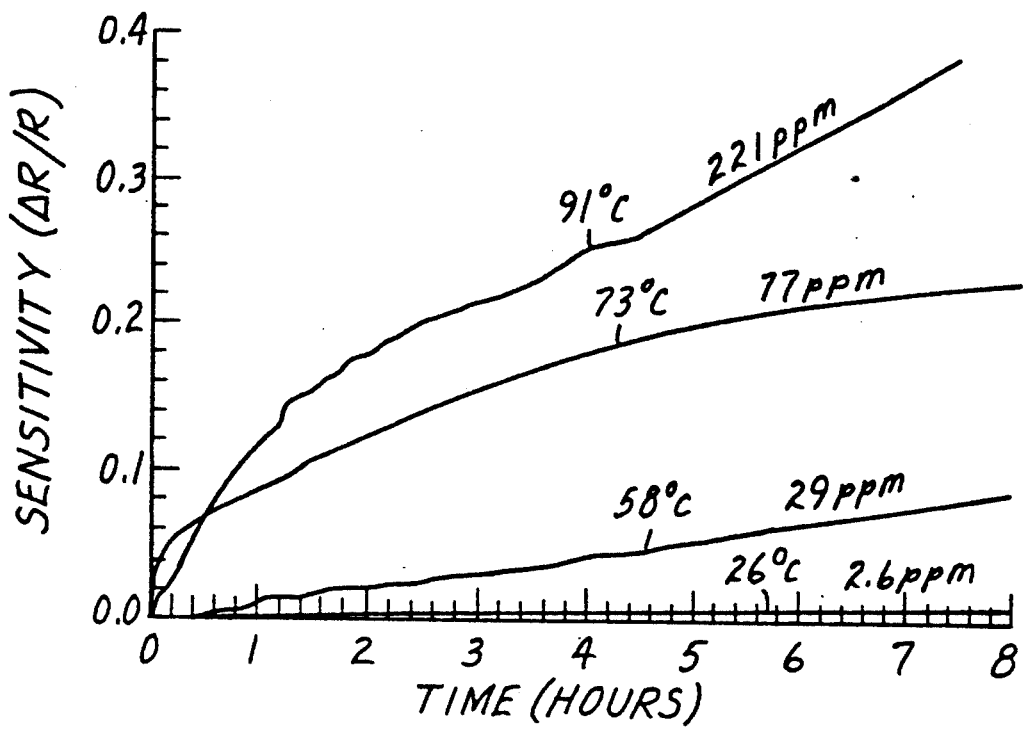
FIG. 12 is the graphic representation of the sensitivity versus time at several temperatures and vapor pressure fractions for type F samples of Example 34.

For Example 34, a type F sample was prepared by vapor coating 1500 Angstroms mass equivalent of gold onto a whisker coated substrate disc, spin coating with NOA 81 optical adhesive (Norland Products, Inc.) at approximately 250 rpm producing a UV cured film approximately 0.3 mm thick. The nanostructured composite was cleanly delaminated from the polyimide substrate. Strips of the composite, approximately 5 mm ×35 mm, were cut and individually mounted inside a test apparatus comprising a sealed 9 oz. glass jar having electrical leads penetrating the jar cover. The initial resistances were in the range of 120 to 600 ohms. The Hg vapor was generated by adding a few milliliters of pure Hg to the apparatus and placing the apparatus assembly into an air oven at controlled temperatures. After a resistance versus time run was complete at one temperature, a new sample strip was used to obtain another run at a new temperature, and hence vapor pressure. The Hg vapor pressure, hence the concentration was taken as the equilibrium vapor pressure of Hg at the given temperature. Four sample strips were exposed in this manner to Hg vapor between room temperature and 91° C. The sensitivity, defined by Equation III is plotted in FIG. 12 and demonstrates a strong temperature dependence and approximately a square root of time dependence, an indication that solid state diffusion is the rate limiting step.

Assuming a model for the gold coated whisker composite as a distribution of gold "posts" which are being converted to a AuHg alloy by solid state diffusion of Hg through the alloy to the alloy/Au interface, which is propagating down the length of the "post" as $t^{\frac{1}{2}}$, the sensitivity can be expressed in terms of the resistivities of the Au and alloy, and a diffusion coefficient of Hg through the alloy. FIG. 18 shows a plot of sensitivity versus reciprocal temperature from which the temperature dependence of the diffusion coefficient can be extracted as shown.

Figure 13:
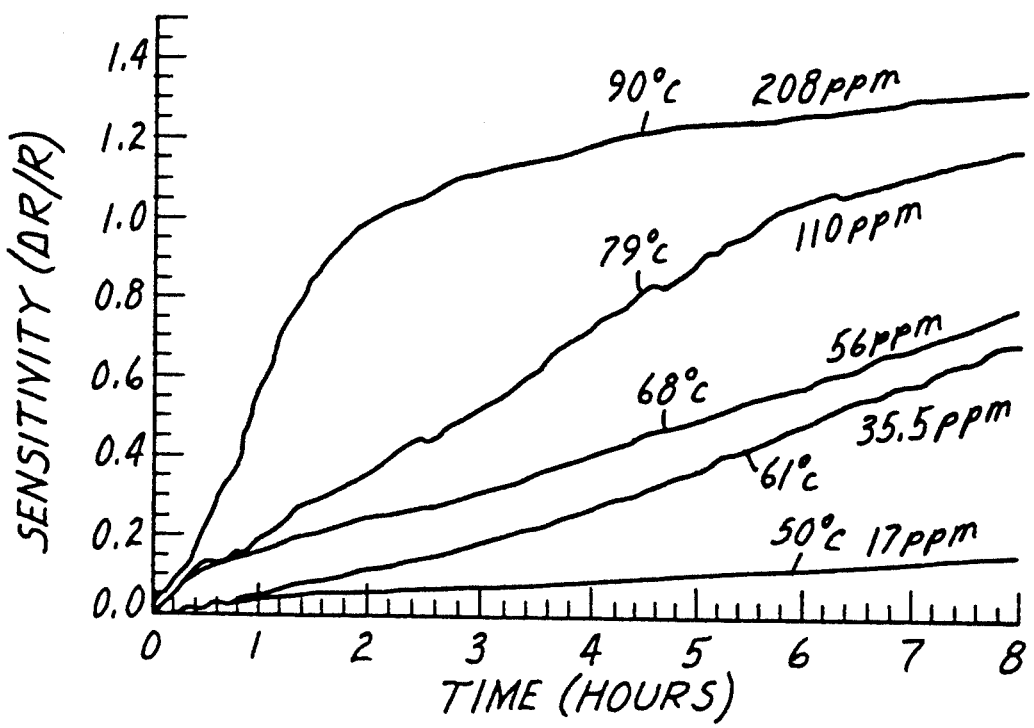
FIG. 13 is the graphic representation of the sensitivity versus time at several temperatures and vapor pressure fractions for type G samples of Example 35.

For Example 35, a type G sample was prepared by vapor coating a mass equivalent of 2500 Angstroms of Au onto a whisker coated substrate, followed by encapsulation in DUCO TM cement by spin coating 4 ml of the adhesive at 440 rpm onto an 8 cm diameter polyimide disc and allowing it to air dry. As in Example 34, strips were cut from the delaminated composite and exposed to mercury vapor at various temperatures. The resistances of the strips were initially in the range of 5 to 20 ohms. For each new temperature, the sample was first monitored in a Hg free apparatus at the designated temperature, establishing that at any temperature the resistance was constant in air. When switched to the Hg containing apparatus, the resistance increased as shown by the sensitivity plot in FIG. 13, wherein a significantly larger response is recorded than with the type F sample in Example 34.

Examples 34 and 35 show that the sensitivity of the sensor for Hg, using Au as the reactive metal, is strongly dependent on the initial sample resistance, assuming the type of polymer is not as important in this case, and that a reaction mechanism can be extracted suggesting solid state diffusion and amalgamation. This implies that even more sensitive Hg vapor sensors could be created with different metal coatings, such as Al, although the Au may be beneficial where no reaction to water vapor or high temperature is desired.

EXAMPLE 36

Example 36 shows that using copper as the conformal coating on the whiskers produces an irreversible sensitive indicator of total water vapor exposure.

Figure 14:
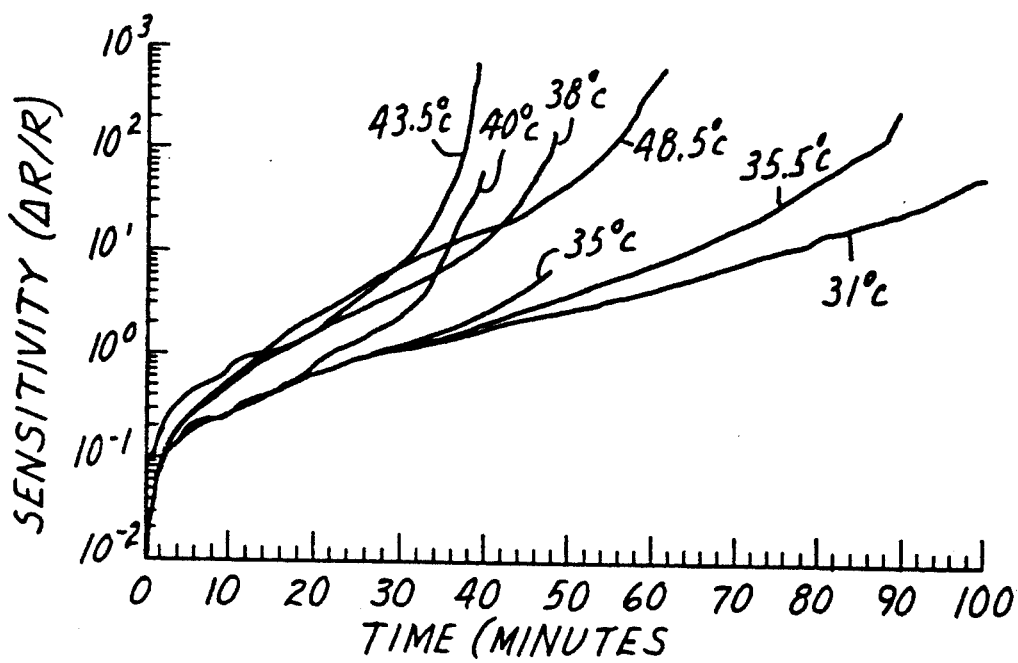
FIG. 14 is the graphic representation of the sensitivity versus time for saturated water vapor at several temperatures for type E samples of Example 36.
Figure 16:
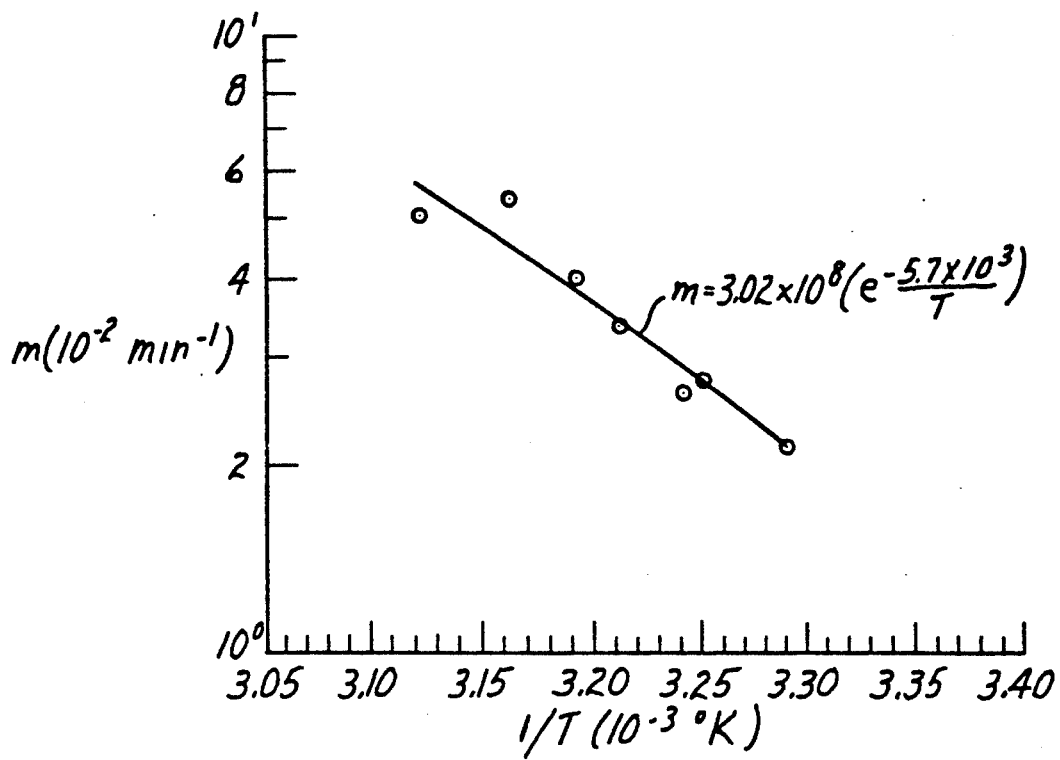
FIG. 16 is an Arrhenius plot for the rate kinetics for water vapor oxidation of Cu coated whisker composite media of type E.

For Example 36, a type E sample was prepared as described in Example 32. Several strips were cut, 2-3 cm long and 6-8 mm wide, having initial resistances in the 50 to a few hundred ohms range. The strips, attached to the leads of an electrometer, were suspended directly over warmed water contained in an insulated Dewar. The resistance change versus time was then recorded for different average water temperatures, the latter generally remaining constant to within 1 degree during the exposure. FIG. 14 shows a summary plot of the sensitivity, $S=(R-R_o)/R_o$, versus time for seven strips at different water temperatures, and hence relative humidities. As indicated, the resistance change can vary over several orders of magnitude as the Cu coating on the whiskers is oxidized. There appear to be at least two regimes of behavior or kinetics, and the mid-range can be modelled assuming an Arrhenius relationship between S and exposure time, $S=S_o\exp(mt)$. Using the slope at the inflection points of the log(S) vs. time curves to get m as a function of temperature, the latter is plotted vs. reciprocal temperature in FIG. 16, from which an apparent heat of enthalpy of only 11 kcal/mole results. This is considerably lower than reported heats of formation of most metal oxides, in the 30–200 kcal/mole range, with Cu approximately 60 kcal/mole. This high reactivity is probably a consequence of the high surface area of the whiskers and small size, which leads to faster response and greater sensitivity than solid thin film based sensors would exhibit.

EXAMPLE 37

Example 37 demonstrates the potential for selecting the polymer encapsulant to specifically sense organic solvent vapors. The gas concentrations were not varied or controlled in these experiments, rather the room temperature vapor pressures were used to simply demonstrate for different metal/polymer combinations that the response can be reversible and that the sensitivity is very dependent on the permeability of the gas or vapor into the encapsulant.

In Example 37, nanostructured film samples were made using four different combinations of metal coating and polymer encapsulant, in addition to that of Example 24. Strips similar to those described in previous Examples were cut from sample discs and electrical contact made to the ends by various means, including crimped indium foil and conductive silver paint. The resistance of each strip was then recorded against time, first with each strip suspended within a dry polyethylene beaker, in air, and then continuing after solvent was added to the bottom of the beaker.

Table 5 summarizes the observed average rate of resistance change for various solvents and indicates whether the response was reversible, when tested over one or two cycles. The total change, expressed as sensitivity S is also given where appropriate. The rate of sensitivity change increases with initial resistivity, since all pieces were about the same size and shape. Also, the affinity of the polymer for the solvent is presumably the primary reason for the large disparity of response of a single sensor type to various solvents.

TABLE 5

| Sample Type | Solvent Vapor | $R_0$ (ohms) | $\Delta R/\Delta t$ (ohms/min) | S (%) | Reversible |
|---|---|---|---|---|---|
| E | MEK | 60 | 0.5 | ~25 | yes |
| E | Acetone | 1000 | 6 | — | — |
| E | Acetone | 8080 | 670 | — | — |
| E | Toluene | 105 | ~0 | — | — |
| E | Toluene | 900 | 1 | — | yes |
| E | Isopropyl Alcohol | 86.5 | 0.025 | — | — |
| K | Acetone | 278 | 18 | — | — |
| K | MEK | 487 | 200–500 | 750 | no |
| K | MEK | 466 | 200–270 | 900 | no |
| J | Acetone | 460 | 22 | 38 | yes |
| J | MEK | 600 | 10 | 72 | yes |
| J | Toluene | 1460 | 40 | 27 | yes |
| J | $C_2F_3Cl_2$ | 1350 | 4 | 6 | yes |
| I | Acetone | 377 | 30 | 300 | yes |

The resistance changes, which in all cases were increases, occur most probably due to both polymer swelling and the attendant increase in inter-whisker spacing, and changes in the intrinsic electronic transport properties of the interwhisker polymer material after sorbing solvent molecules. Similar resistance changes in three dimensional dispersions of carbon black particles in polymers is well known and often described in terms of percolation theory and the Hildebrand solubility parameter of the polymer and solvent. It is also conceivable that the polymer/metal interface of the coated whiskers is a controlling factor in charge injection or tunneling as well. The potential to tailor the polymer and metal combination for desired responses from specific gases or vapors would appear feasible. The results suggest, as with $H_2S$, that the rate of sensitivity change may be correlatable with vapor concentration.

EXAMPLE 38

Example 38 demonstrates the use of the composite medium as a liquid analyte sensor.

A piece of type B sample, 6 mm ×40 mm, was held in the form of a semicircle by the electrical leads from an electrometer and immersed in a 180 ml volume of distilled water, contained in a 250 ml glass jar, so that the electrical clip leads were just above the water surface. The initial air resistance, 149.3 ohms, did not change when immersed in the water, until after several minutes, at which time the resistance began to slowly decrease at a constant rate of 0.26 ohms/min. over a period of 45 minutes. At this point, 1 milliliter of an equilibrium solution of $Br_2$ in distilled water was injected by syringe into the center of the 180 ml sample volume and briefly stirred, giving a 68 ppm aqueous Br solution. The resistance remained stable for approximately 2 minutes, then began rapidly decreasing at a rate of approximately 4 ohms/min., finally equilibrating after fifteen minutes for a total sensitivity change of 26%.

EXAMPLE 39

Example 39 demonstrates that the capacitance measured perpendicular to the film plane can be used as the sensor property.

Figure 15:
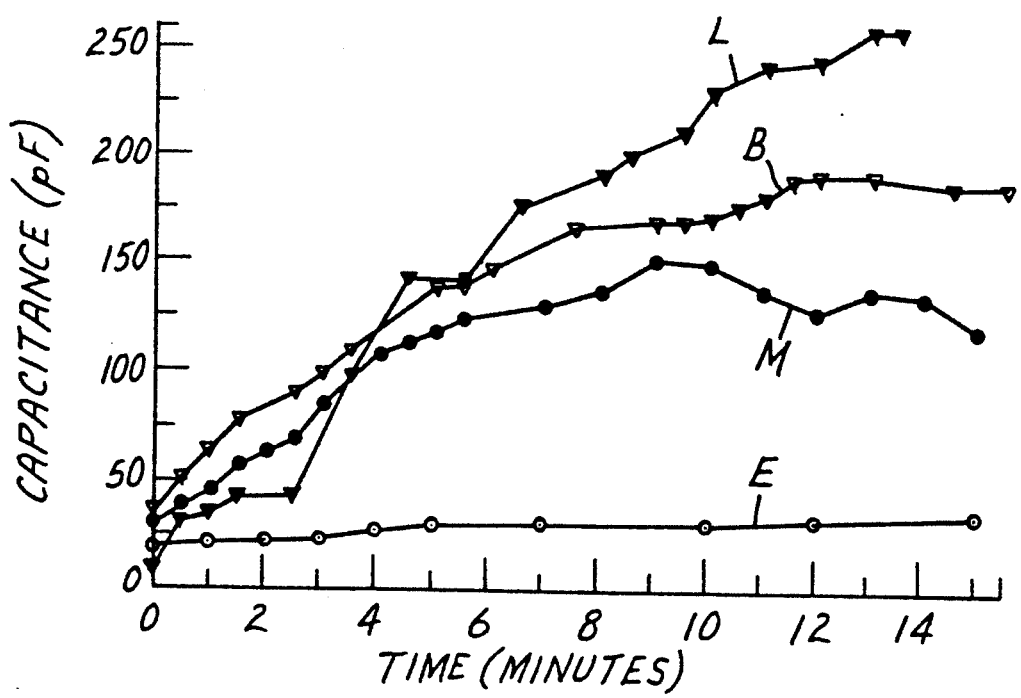
FIG. 15 is the graphic representation of the capacitance change versus time for B, E, L, and M type samples of Example 40.

Small area pieces, on the order of 2 cm$^2$, were cut from B, E, L, and M type samples. Aluminum foil backed adhesive tape was applied to the polymer encapsulant side of each piece so as to form a simple capacitor with the nanostructured surface of the composite forming one conductive side of the capacitor and the aluminum foil the other. The thickness of the adhesive layer on the tape was much thinner than the composite film, the latter being in the 0.05 to 0.125 mm thickness range. Electrical contact to the formed capacitor was made by smooth jawed alligator clips. To measure the capacitance, a 1.025 megohm resistor was placed in series with the sample capacitor, a squarewave signal in the 100 Hz to several kHz range was applied across the two circuit elements, and the voltage signal across the sample capacitor was monitored with an oscilloscope. The RC time constant was read directly from the sample capacitor waveform, and the sample's capacitance calculated from Equation I. The sample test assembly was then placed in a covered beaker, directly over acetone liquid in the bottom, to expose the sample capacitor to a nominally saturated vapor. The RC time constant was then periodically read off the oscilloscope, the total circuit capacitance calculated and the scope probe capacitance subtracted to give the sample capacitance. FIG. 15 shows the variation of sample capacitance with elapsed time for the four sample types, beginning at t=0 when the samples were placed in the vapor.

By combining the capacitance property of the Example with the demonstrated surface resistance properties of Example 37, it is clear that the sensor media could be made into a resonant, tuned circuit element with a fast frequency shift type response.

Various modifications and alterations of this invention will become apparent to those skilled in the art without departing from the scope and spirit of this invention, and it should be understood that this invention is not to be unduly limited to the illustrative embodiments set forth herein.

I claim:

1. A composite article with an electrically conductive surface, comprising an encapsulating layer having a regular or random array of discrete microstructures, each microstructure comprising an organic compound wherein the molecule thereof is planar and comprises claims or rings over which $\pi$-electron density is extensively delocalized and an optional conformal coating enveloping said whisker-like structure, wherein said array of discrete microstructures is encapsulated in said encapsulating layer, such that one end of each microstructure is embedded within said encapsulating layer and the other end of each microstructure is exposed and coincident with the surface of said encapsulating layer.

2. The composite article according to claim 1, wherein said organic material is selected from the group consisting of polynuclear aromatic hydrocarbons and heterocyclic aromatic compounds.

3. The composite article according to claim 2, wherein said organic material is selected from the group consisting of perylenes, phthalocyanines, and porphyrins.

4. The composite article according to claim 3, wherein said organic material is N,N'-di(3,5-xylyl)perylene-3,4:9,10 bis(dicarboximide).

5. The composite article according to claim 1, wherein said conformal coating is a conducting material selected from a group consisting of metals, inorganic compounds, and conducting polymers.

6. The composite article according to claim 5, wherein said metal is selected from the group consisting of aluminum, cobalt, cobalt chromium, nickel, nickel chromium, platinum, silver, gold, iron, copper and other transition metals.

7. The composite article according to claim 1, wherein said encapsulating material is organic or an inorganic material.

8. The composite article according to claim 7, wherein said organic material is selected from the group consisting of organic pigments, thermoplastic polymers and co-polymers derived from olefins and other vinyl monomers, condensation and addition polymers, and natural polymers and their derivatives.

9. The composite article according to claim 7, wherein said inorganic material is selected from the group consisting of gels, sols, or semiconductor, or metal oxides.

10. The composite article according to claim 1, wherein capacitive impedance is measured perpendicular to the surface plane of said article and resistive impedence is measured parallel to the surface plane of said article.

11. A sensor comprising the composite article in accordance with claim 1, wherein said conformal coating, said encapsulating material and said whisker-like structures are independently selected for their responsiveness to gas, vapor, or liquid analytes.

12. A flexible thin film according to claim 11.

13. The composite article according to claim 4, wherein said organic pigments are selected from the group consisting of perylene red, phthalocyanine, and porphyrins.

14. The composite article according to claim 8, wherein said thermoplastic polymers and co-polymers are selected from the group consisting of polyesters, polyimides, polyamides, polyethers, polyurethanes, and polyureas.

* * * * *

UNITED STATES PATENT AND TRADEMARK OFFICE
CERTIFICATE OF CORRECTION

PATENT NO. : 5,238,729
DATED : August 24, 1993
INVENTOR(S) : Debe

It is certified that error appears in the above-identified patent and that said Letters Patent is hereby corrected as shown below:

ON THE TITLE PAGE :

In the title, Replace "Nanosstructured" with —Nanostructured—

Col. 1, line 2, Replace "Nanosstructured" with —Nanostructured—

Col. 1, line 15, Replace "Background Art" with —Background of the Invention—

Col. 6, line 16, Delete the dash after "face of the"

Col. 8, line 38, Delete ", are a" between 16 submicrometer

Col. 9, line 2, Insert —range— between "the from"

Col. 19, line 24, Delete "and 2" after Example 6

Col. 28, line 21, Replace "claim 4" with —claim 8—

Signed and Sealed this

Fourth Day of July, 1995

Attest:

BRUCE LEHMAN

Attesting Officer     Commissioner of Patents and Trademarks